United States Patent [19]

Ladanyi et al.

[11] Patent Number: 5,670,317
[45] Date of Patent: Sep. 23, 1997

[54] DIAGNOSTIC TEST FOR THE DESMOPLASTIC SMALL ROUND CELL TUMOR

[75] Inventors: Marc Ladanyi, New York; William Gerald, Pelham, both of N.Y.

[73] Assignee: Sloan-Kettering Institute for Cancer Research, New York, N.Y.

[21] Appl. No.: 437,027

[22] Filed: May 8, 1995

[51] Int. Cl.$^6$ .............................. C12Q 1/68; C12P 19/34; C07H 21/04

[52] U.S. Cl. .......................... 435/6; 435/91.2; 435/91.5; 435/91.51; 536/23.4; 536/23.5; 536/24.31; 436/64; 935/9; 935/78

[58] Field of Search .......................... 435/6, 91.2, 91.5, 435/9.51; 536/23.5, 23.4, 24.31; 935/77, 78, 9; 436/64

[56] References Cited

PUBLICATIONS

Gerald et al, The American Journal of Human Genetics (Sep. 1994) 55:A57, abstract 305.
Barr et al, Journal of the American Medical Association (Feb. 195) 273: 553–557.
Bickmore, W.A., Oghene, K., Little, M., Seawright, A., van Heyningen, V. & Hastie, N.D. (1992) Science, 257:235–237.
Biegel, J.A., Conard, K. and Brooks, J.J. (1993) Genes Chromosom. Cancer, 7:119–121.
Brenner, B., Wildhardt, G., Schneider, S. and Roger–Pokora, B.(1992) Oncogene, 7:1431–1433.
Call, K.M., Glaser, T., Ito, C.Y., Buckler, A.J., Pelletier, J., Haber, D.A., Rose, E.A., Kral, A., Yeger, H., Lewis, W.H., Jones, C. and Housman, D.E. (1990) Cell, 60:509–520.
Crozat, A., Aman, P., Mandahl, N. and Ron, D. (1993) Nature, 363:640–644.
Davis, R.J., D'Cruz, C.M., Lovell, M.A., Biegel, J.A., Barr, F.G. (1994) Cancer Research, 54:2869–2872.

Delattre, O., Zucman, J., Plougastel, B., Desmaze, C., Melot, T., Peter, M., Kovar, H., Joubert, I., de Jong, P., Rouleau, G., Aurias, A. and Thomas, G. (1992) Nature, 359:162–165.
Downing, J.R., Head, D.H., Parham, D.M., Douglass, E.C., Hulshof, M.G. Link, M.P., Motroni, T.A., Grier, H.E., Curcio–Brint, A.M. and Shapiro, D.N. (1993) Am. J. Pathol., 143:1294–1300.
Drummond, I.A., Madden, S.L., Rohwer–Nutter, P., Bell, G.I., Sukhatme, V.P. and Rauscher, F.J. III. (1992) Science, 257:674–678.
Galili, N., Davis, R.J., Fredericks, W.J., Mukhopadhyay, S., Rauscher F.J. III, Emanuel B.S., Rovera, g. and Barr, F.G. (1993) Nature Genet., 5:230–235.
Gerald, W.L., Chao, J. and Chao, L. (1986) Biochimica et Biophysica Acta (N), 866:1–14.
Gerald, W.L., Miller, H.K., Battifora, H., Miettinen, M., Silva, E.G. and Rosai, J. (1991) Am. J. Surg. Pathol., 15:499–513.

(List continued on next page.)

Primary Examiner—Carla J. Myers
Attorney, Agent, or Firm—John P. White

[57] ABSTRACT

The present invention provides an isolated nucleic acid molecule encoding a chimeric EWS-WT1 protein. This invention also provides an isolated protein which is a chimeric EWS-WT1 protein. This invention further provides a method of diagnosing a desmoplastic small round cell tumor in a subject which comprises detecting in a sample from the subject a nucleic acid molecule encoding a chimeric EWS-WT1 protein, positive detection indicating the presence of desmoplastic small round cell tumor. This invention also provides a method of inhibiting the growth of a neoplastic cell, wherein the cell is characterized by the presence of a chimeric EWS-WT1 protein which comprises contacting an antibody which specifically recognizes the chimeric EWS-WT1 fusion protein under suitable conditions so that an antibody-antigen complex is formed, thereby inhibiting the growth of the neoplastic cell.

11 Claims, 11 Drawing Sheets

OTHER PUBLICATIONS

Gerald, W.L. and Rosai, J. (1993) Zentralbl. Pathol., 139:141–152.

Gerald, W.L. and Rosai, J., Case 2. (1989) Pediatr. Pathol. 9:177–183.

Gerald, W.L., Rosai, J. and Ladanyi, M. (1995) Proc. Natl. Acad. Sci. U.S.A., 92:1028–1032.

Gessler, M., Konig, A. and Bruns, G.A.P. (1992) Genomics, 12:807–813.

Haber, D.A., Sohn, R.L., Buckler, A.J., Pelletier, J., Call, K.M. and Houseman, D.E. (1991) Proc. Natl. Acad. Sci., U.S.A., 88:9618–9622.

Ladanyi, M. and Gerald, W. (Jun., 1994) Cancer Res. 54:2837–2840.

Ladanyi, M., Lewis, R., Garin-Chesa, P., Rettig, W.J., Huvos, A.G., Healy, J.H. and Jhanwar, S.C. (1993) Diag Mol. Patho., 2:141–146.

Madden, S.L., Cool, D.M., Morris, J.F., Gashler, A., Sukhatme, V.P. and Rauscher, F.J. III (1991) Science, 253:1550–1553.

Ordonñez, N.G., El–Naggar, A.K., Ro, J.Y., Silva, E.G. and MacKay, B. (1993) Hum. Pathol., 24:850–865.

Ordoez, N.G., Zirkin, R. and Bloom, R.E. (1989) Am. J. Surg. Pathol., 13:413–421.

Plougastel, B.,Zucman, J., Peter, M., Thomas, G. and Delattre, O. (1993) Genomics, 18:609–615.

Rauscher, F.J. III, Benjamin, L.E., Fredericks, W.J. and Morris, J.F. (May 25, 1995) Cold Spring Harbor on Quantitative Biology, The Molecular Genetics of Cancer, vol. 59:137–145.

Rauscher, F.J. III, Morris, J.F. Tournay, O.E., Cook, D.M. and Curran, T. (1990) Science, 250:1259–1262.

Rodriquez, E., Sreekantaiah, C., Gerald, W., Reuter, V.E., Motzer, R. J. and Chaganti, R.S.K. (1993) Cancer Genet. Cytogenet. 69:17–21.

Sawyer, J.R., Tryka, A.F. and Lewis, J.M. (1992) A. J. Surg. Pathol., 16:411–416.

Shen, W.P., Towne, B. and Zadeh, T.M. (1992) Cancer Genet. Cytogent., 64:189–191.

Sorensen, P.H.B., Lessnick, S.L., Lopez–Terrada, D., Liu, X.F., Triche, T.J. and Denny, C.T. (1994) Nature Genet., 6:146–151.

Tadokoro, K., Oki, N., Fujii, H., Ohshima, H., Inoue, T. and Yamada, M., (1992) Jpn. J. Cancer Res., 83:1198–1203; and.

Zucman, J., Melot, T., Desmaze, C., Ghysdael, J., Plougastel, B., Peter, M., Zucker, J.M., Triche, T.J., Sheet, D., Turc–Carel, C. Ambros, P., Combaret, V., Lenoir, G., Aurias, A., Thomas, G. and Delattre, O. (1993) EMBO Journal, 12:4481–4487.

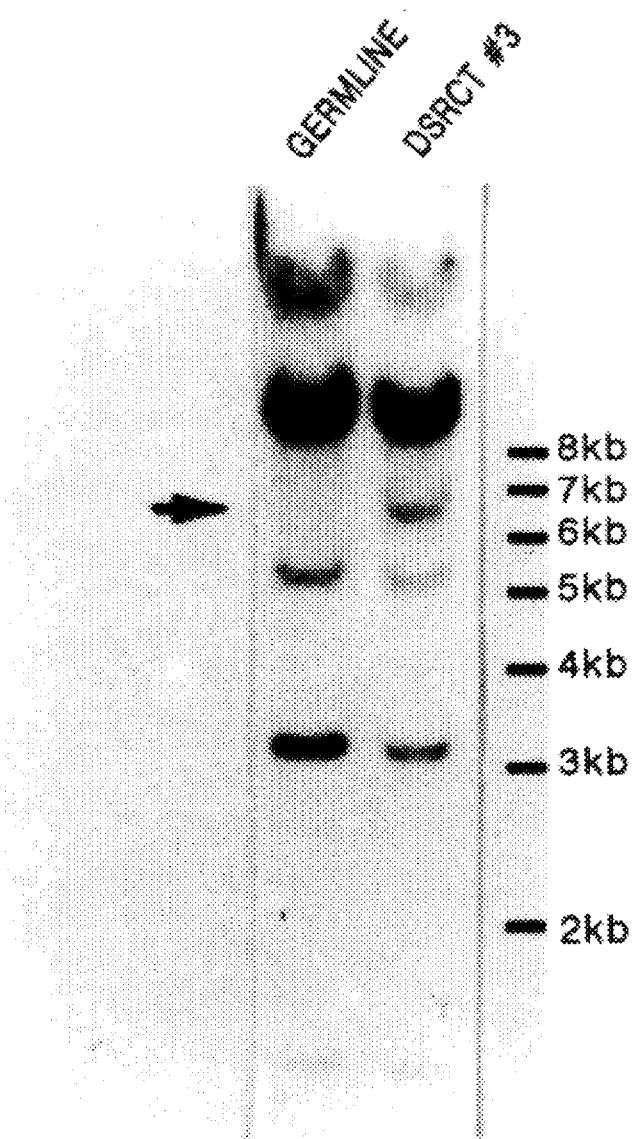

FIG. 7B

```
TCCTACAGCCAAGCTCCAAGTCAATATAGCCAACAGAGCAGCTACGGG      51
 S  Y  S  Q  A  P  S  Q  Y  S  Q  Q  S  S  S  Y  G

EWS exon 7   WT1 exon 8
          _____
CAGCAGAGTGAGAAACCATACCAGTGTGACTTCAAGGACTGTGAACGAAGG   102
 Q  Q  S  E  K  P  Y  Q  C  D  F  K  D  C  E  R  R TTTCTCGTTCAGACCAGCTCAAAAGACTCAAAAGGAGACATACAGGTGTG   153
 F  S  R  S  D  Q  L  K  R  H  Q  R  R  H  T  G  V AAACCATTCCAGTGTAAAACTTGTCAGCGAAAGTTCTCCCGGTCCGACCAC   204
 K  P  F  Q  C  K  T  C  Q  R  K  F  S  R  S  D  H CTGAAGACCCACACCAGGACTCATACAGGTAAAACAAGTGAAAAGCCCTTC   255
 L  K  T  H  T  R  T  H  T  G  K  T  S  E  K  P  F

AGCTGTCGGTGGC                                          268
 S  C  R  W
```

DIAGNOSTIC TEST FOR THE DESMOPLASTIC SMALL ROUND CELL TUMOR

The invention disclosed herein was made with Government support under NCI Core Grant No. 08748 from the Department of Health and Human Services. Accordingly, the U.S. Government has certain rights in this invention.

Throughout this application, various references are referred to within parentheses. Disclosures of these publications in their entireties are hereby incorporated by reference into this application to more fully describe the state of the art to which this invention pertains. Full bibliographic citation for these references may be found at the end of this application, preceding the sequence listing and the claims.

BACKGROUND OF THE INVENTION

Small round cell tumors of childhood are a diagnostic challenge to the surgical pathologist. They constitute a family of biologically aggressive tumors occurring in children and adolescents, that share several morphologic features and are often difficult to distinguish from each other. Accurate diagnosis is essential to institute appropriate therapy and predict prognosis.

Consistent cytogenetic alterations have been identified in several members of this family, including a t(2;13)(q35;q14) translocation in alveolar rhabdomyosarcoma (Barr et al., 1993), a t(11;22)(q24;q12) translocation in Ewing's sarcoma/peripheral neuroectodermal tumor (PNET) (Whang-Peng et al., 1984), and primitive neuroectodermal tumor (Aurias et al., 1983; Turc-Carel et al., 1983; Whang-Peng et al., 1984; Turc-Carel et al., 1988; Turc-Carel et al., 1986; Douglass et al., 1987; and Wang-Wu et al., 1988). Recently, these chromosomal translocations have been characterized at the molecular level and found to result in EWS-FLI-1 and EWS-ERG gene fusions in Ewing's sarcoma/PNET (Downing et al., 1993 and Delattre et al., 1992), and PAX3-FKHR or PAX7-FKHR in alveolar rhabdomyosarcoma (Galili et al., 1993 and Davis et al., 1994).

Characterization of translocation breakpoints has frequently revealed fusion of genes encoding potential transcription factors or other nucleic acid binding proteins with generation of chimeric products (Delattre et al., 1992; Crozat et al., 1993; Zucman et al., 1993; Galili et al., 1993 and Sorensen et al., 1994). These fusion proteins are postulated to juxtapose an effector domain from one translocation partner to the nucleic acid binding domain of the other, resulting in a novel function that contributes to tumorigenesis. Chimeric transcripts and gene fusions specific for each translocation can be detected in clinical samples by Reverse Transcriptase PCR (RT-PCR) and fluorescent in situ hybridization (FISH), and may prove to be a reliable and very useful diagnostic technique in the small round cell tumor family, because conventional karyotyping for these tumors is often unsuccessful (Downing et al., 1993).

Desmoplastic small round cell tumor (DSRCT) is a recently recognized entity (Gerald and Rosai, 1989; Ordonez et al., 1989; and Gerald et al., 1991) that affects mainly children and adolescent males, usually in the form of widespread intraabdominal growth not related to any organ system. Histologically, it is characterized by angulated nests of small round cells within an abundant desmoplastic stroma. The tumor cells show multiphenotypic differentiation, expressing epithelial, muscle, and neural markers (Gerald and Rosai, 1989).

Karyotypes have been reported in five cases of DSRCT; in four of these five cases, a clone with a breakpoint in the 22q11.2-13 region was present, in three cases as the translocation t11;22)(p13;q11.2-12) (Sawyer et al.,1992; Shen et al., 1992; Biegel et al., 1993 and Rodriguez et al., 1993). Band 22q12 is the site of the EWS gene, which is rearranged in the tumor-specific translocations, t11;22)(q24;q12) and t(12;22)(q13;q12), of ES and CCS (a.k.a. malignant melanoma of soft parts), respectively (Delattre et al., 1992 and Zucman et al., 1993). In light of the karyotypic data and the involvement of the EWS gene in two other primitive sarcomas, the configuration of the EWS gene in DSRCT was examined. At 11p13, WT1 was screened as a candidate breakpoint locus, because of its involvement in Wilms' tumor, which shares some histopathologic features of DSRCT, and because it codes for a transcription factor, like other translocation partners of EWS (Delattre et al., 1992 and Zucman et al., 1993).

SUMMARY OF THE INVENTION

The configuration of the EWS and the WT1 genes in DSRCT were initially examined in five DSRCT tissue samples. The results confirmed the presence of a consistent fusion of the EWS and WT1 genes in DSRCT, resulting in a chimeric EWS-WT1 RNA.

Probes for the EWS gene were used to isolate a genomic DNA junction fragment from a DSRCT and characterized the breakpoint region. Polymerase chain reaction (PCR) analysis of RNA from DSRCT reveals that chimeric transcripts are expressed and encode a predicted protein product that links the amino terminal domain of EWS to either of alternatively spliced forms of the zinc-finger DNA-binding domain of WT1. The potential transcript from the reciprocal WT1-EWS gene fusion is not detectable. DSRCT therefore represents the third tumor type to be associated with a chromosomal translocation involving the EWS gene and the only tumor associated with consistent translocation of WT1. The proposed product of the chimeric transcript, joining domains from two different tumor-associated genes, is implicated in the genesis of a distinctive tumor type.

The specificity and sensitivity of the molecular detection of EWS-WT1 chimeric transcripts by RT-PCR were further assessed along with its potential utility in the differential diagnosis of the DSRCT from other developmental tumors. Twelve DSRCT and forty nine other developmental tumors associated with related genetic abnormalities and considered in the differential diagnosis of DSRCT, were analyzed using a panel of primer pairs that distinguish specific chimeric transcripts.

The present invention provides an isolated nucleic acid molecule encoding a chimeric EWS-WT1 protein. This invention also provides an isolated protein which is a chimeric EWS-WT1 protein. This invention further provides a method of diagnosing a desmoplastic small round cell tumor in a subject which comprises detecting in a sample from the subject a nucleic acid molecule encoding a chimeric EWS-WT1 protein, positive detection indicating the presence of desmoplastic small round cell tumor. This invention also provides a method of inhibiting the growth of a neoplastic cell, wherein the cell is characterized by the presence of a chimeric EWS-WT1 protein which comprises contacting an antibody which specifically recognizes the chimeric EWS-WT1 fusion protein under suitable conditions so that an antibody-antigen complex is formed, thereby inhibiting the growth of the neoplastic cell. dr

Figure 2:
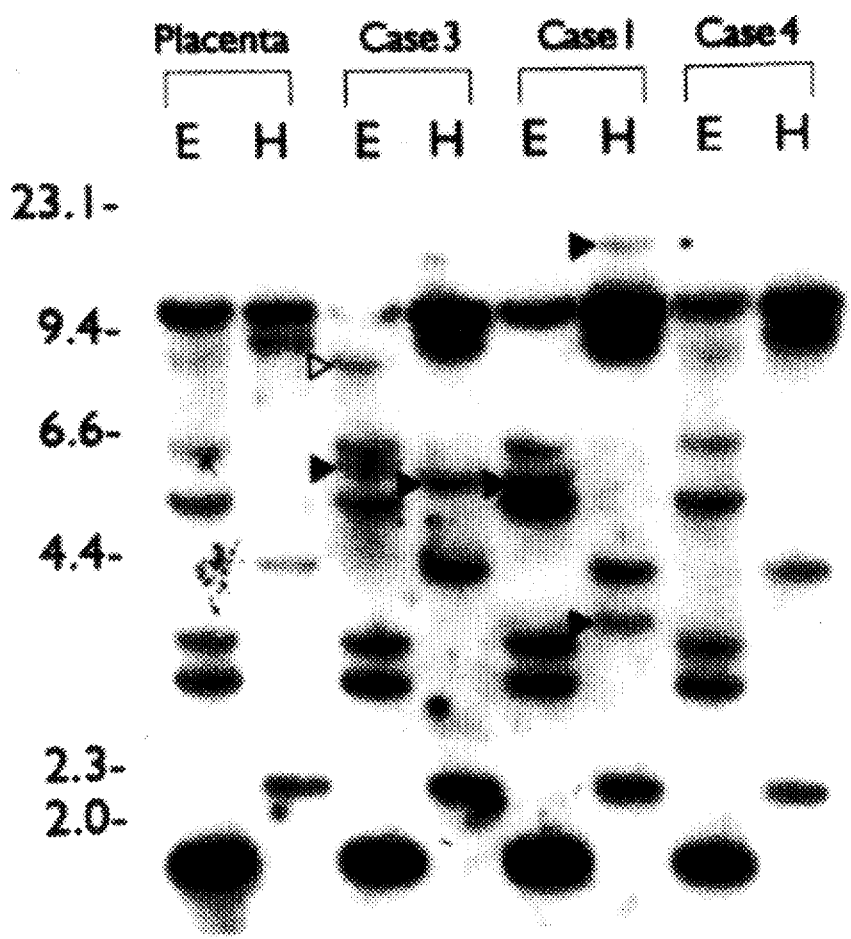

and HindIII (H) digests with this EWS partial cDNA probe is seen in the lanes containing placental DNA. The approximate sizes in kilobases of HindIII-digested lambda DNA are indicated on the left. Rearranged bands are seen with both enzymes in cases 1 and 3 of EXAMPLE 1 (black and white triangles). The black triangles indicate rearranged bands which comigrate with rearranged WT1 bands (FIG. 2). Case 4 showed only germline bands.

Figure 1:
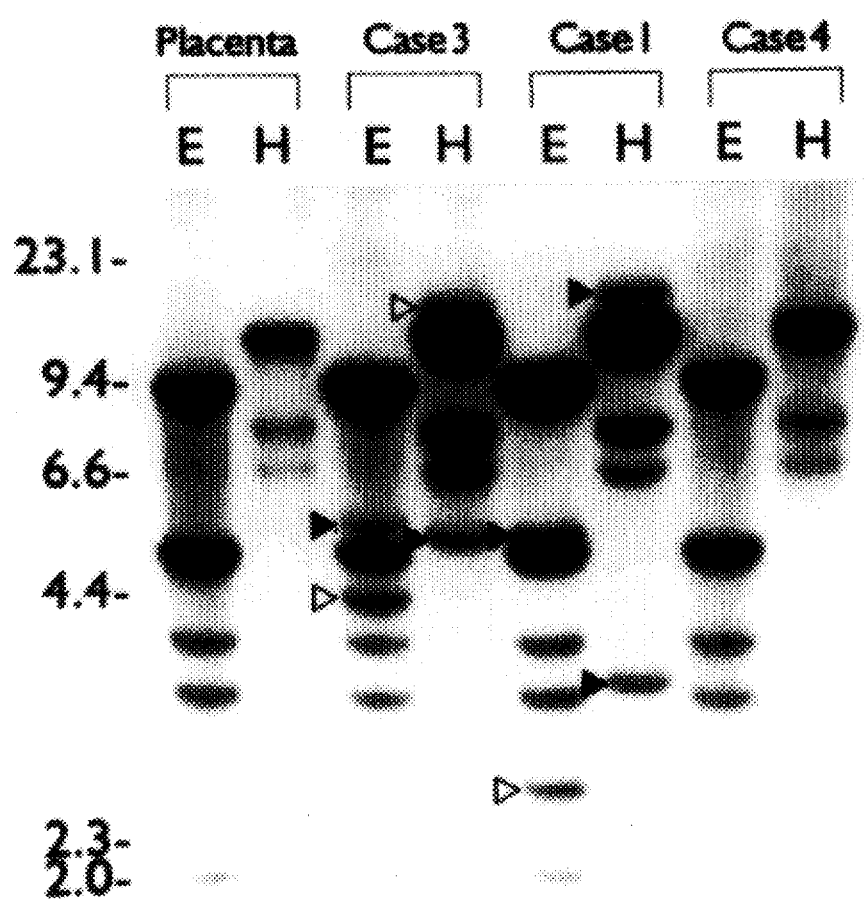
FIG. 1 is a Southern blot detection of EWS rearrangement in DSRCT. The normal germline band pattern for EcoRI (E)

FIG. 2 is a Southern blot detection of WT1 rearrangement in DSRCT. Re-hybridization of same blot as in FIG. 1 with a WT1 cDNA probe. The normal germline band pattern for EcoRI (E) and HindIII (H) is seen in the lanes containing placental DNA. The approximate sizes in kilobases of HindIII-digested lambda DNA are indicated on the left. Rearranged bands are seen with both enzymes in cases 1 and 3 of EXAMPLE 1 (black and white triangles). The black triangles indicate rearranged bands which comigrate with rearranged EWS bands (FIG. 1). Case 4 of EXAMPLE 1 showed no WT1 rearrangement.

Figure 3:
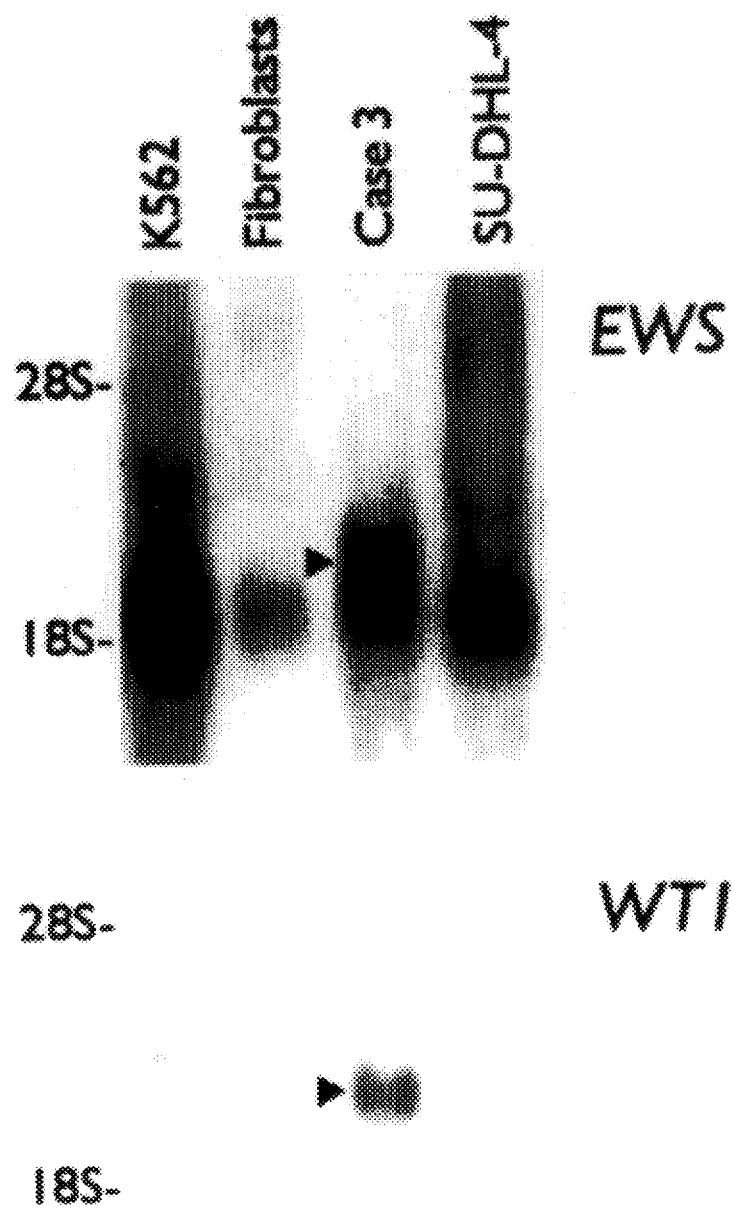

FIG. 3 is a Northern blot analysis of EWS and WT1 in case 3 od EXAMPLE 1. The positions of the 18S and 28S ribosomal RNA bands are indicated on the left. Approximately 10 ug of total RNA from acute myeloid leukemia cell line K562, cultured fibroblasts, case 3, and B-cell lymphoma cell line SU-DHL-4 were electrophoresed. Ubiquitous expression of the 2 kb EWS transcript is seen in all samples. In addition, case 3 of EXAMPLE 1 appears to show an aberrant EWS transcript, approximately 2.5 kb in size (triangle). Re-hybridization of the same filter with a WT1 probe shows expression only in cell line K562 and case 3 of EXAMPLE 1. The expression of WT1 in cell line K562 has been previously reported (Call et al., 1990). The transcript in K562 is of normal size (3 kb). The transcript in case 3 (triangle) is abnormally small (approximately 2.5 kb) and appears to comigrate with the aberrant EWS transcript.

Figure 4:
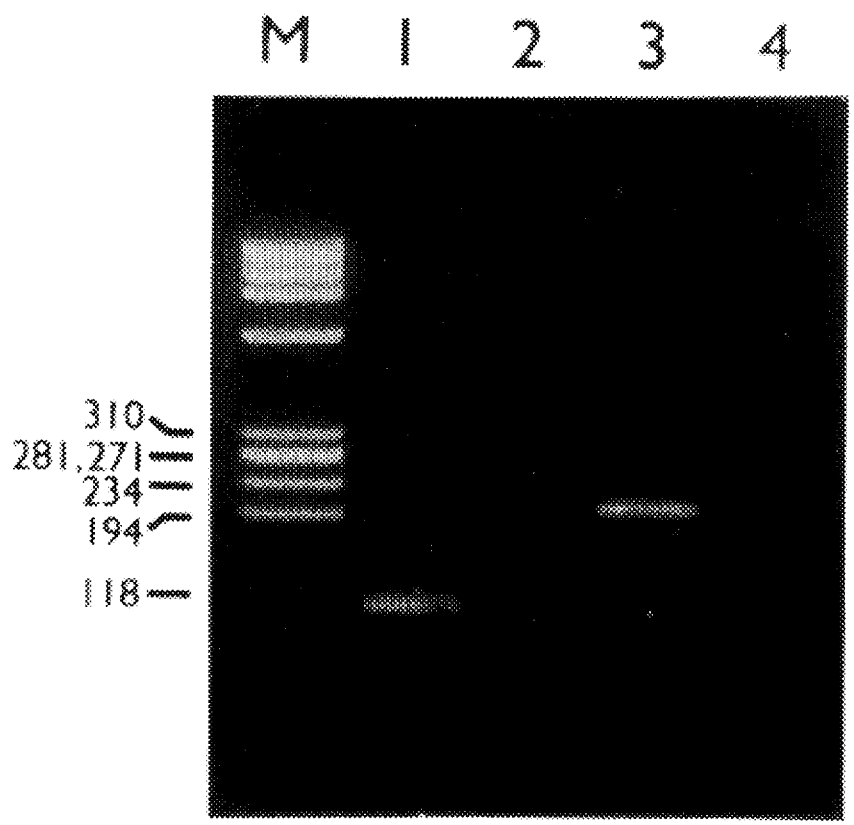

FIG. 4 is an RT-PCR analysis of chimeric EWS-WT1 mRNA in case 3 of EXAMPLE 1. The reactions in lanes 1 and 3 were performed on 1 ug of total RNA from case 3 of EXAMPLE 1. The reactions in lanes 2 and 4 were carried out in the absence of RNA. Lanes 1 and 2 used the EWS primer (SEQUENCE ID NO. 1) in combination with WT1 exon 8 primer (SEQUENCE ID NO. 16), and lanes 3 and 4 used the EWS primer (SEQUENCE ID NO. 16) in combination with WT1 exon 9 primer (SEQUENCE ID NO. 17). Lane M contains a DNA size marker, HaeIII-digested PhiX174 DNA (sizes of selected bands indicated in bp). In case 3 of EXAMPLE 1, a single PCR product was seen with each primer pair (lanes 1 & 3). The sizes of the products were consistent with a junction of EWS exon 7 to WT1 exon 8. PCR products of the same size were also obtained in case 1 of EXAMPLE 1 with the same primer sets, but no products were seen with RNA from acute myeloid leukemia cell line K562.

FIG. 5A shows the detection and cloning of EWS-WT1 junction fragment from DSRCT. Southern blot analysis of DNA from DSRCT that was used in construction of size-selected genomic library. Nongermline BamHI restriction fragment is detected with EWS probe (arrow).

Figure 5B:
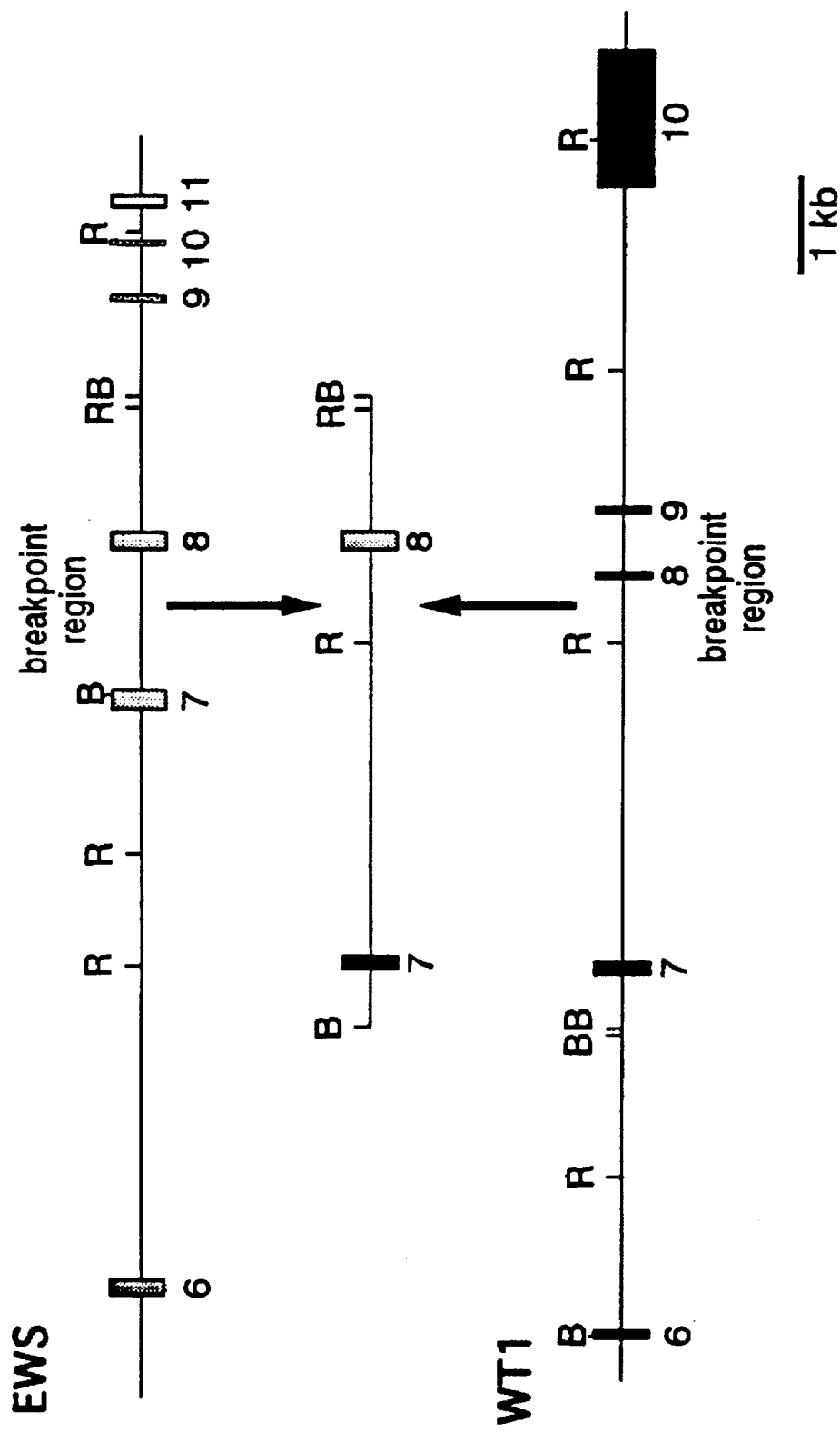

FIG. 5B shows the EcoRI (R) and BamHI (B) restriction map of cloned junction fragment compared to corresponding regions of wild type WT1 and EWS gene maps (Haber et al., 1991; Tadokoro et al., 1992 and Plougastel et al., 1993). Exons are represented as boxes and numbered. Sites of breakpoints are indicated by arrows.

Figure 6:
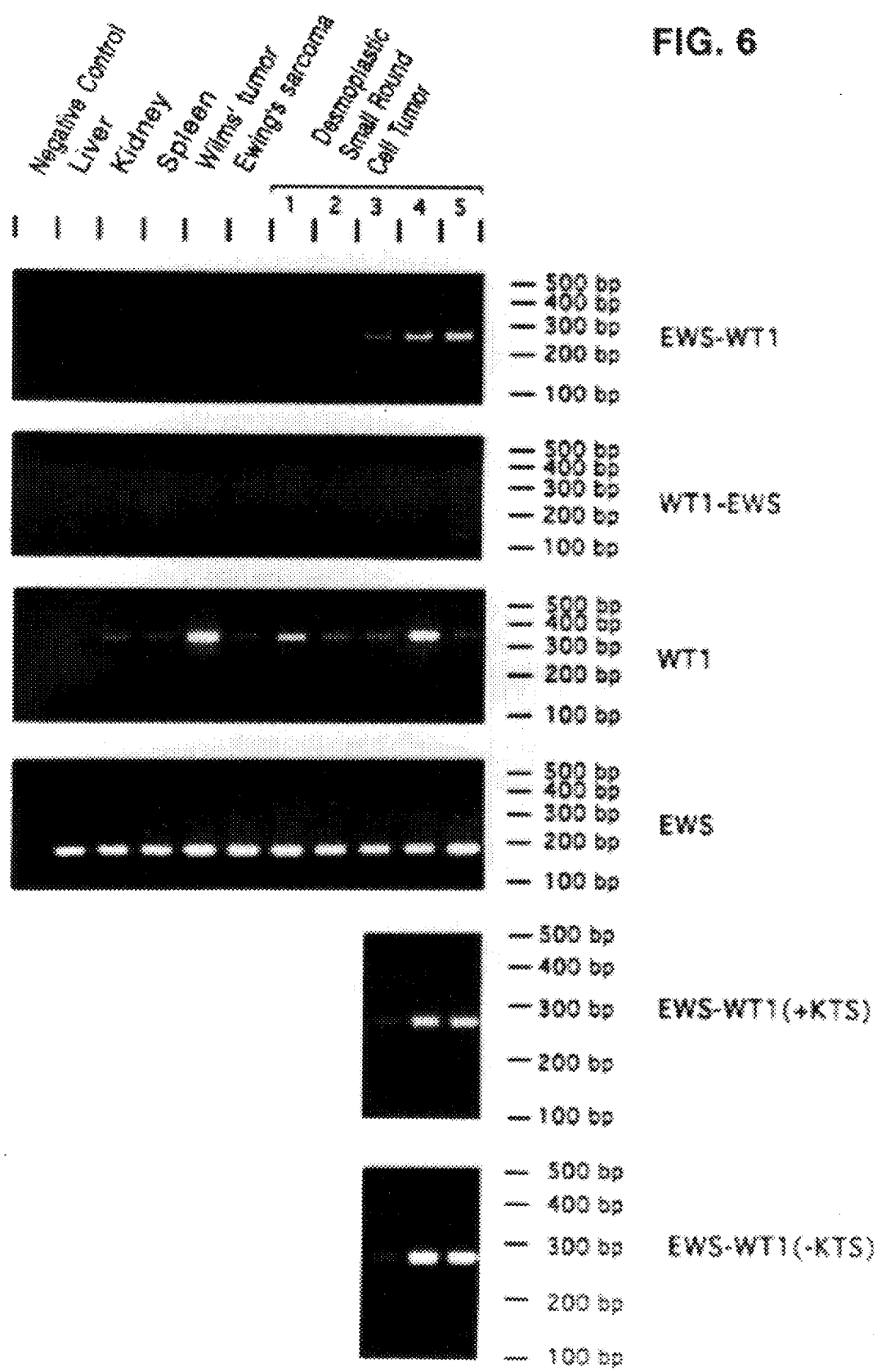

FIG. 6 is an RT-PCR analysis of DSRCT for chimeric and wild-type transcripts. Each panel is a photograph of the ethidium bromide stained agarose gel on which products of PCR reaction were electrophoresed. Migration position of size markers are indicated at the right of each panel. Labels at the top of each lane indicate source of RNA. Negative control lanes are reactions carried out in the absence of added template. Labels at the right indicate the expected transcript. Primers used are described in the text. RNA isolated from DSRCT case 3, 4, and 5 of EXAMPLE 2 yield chimeric EWS-WT1 products by RT-PCR and both alternatively spliced forms (+and −KTS) are detected in these three cases.

Figure 7A:
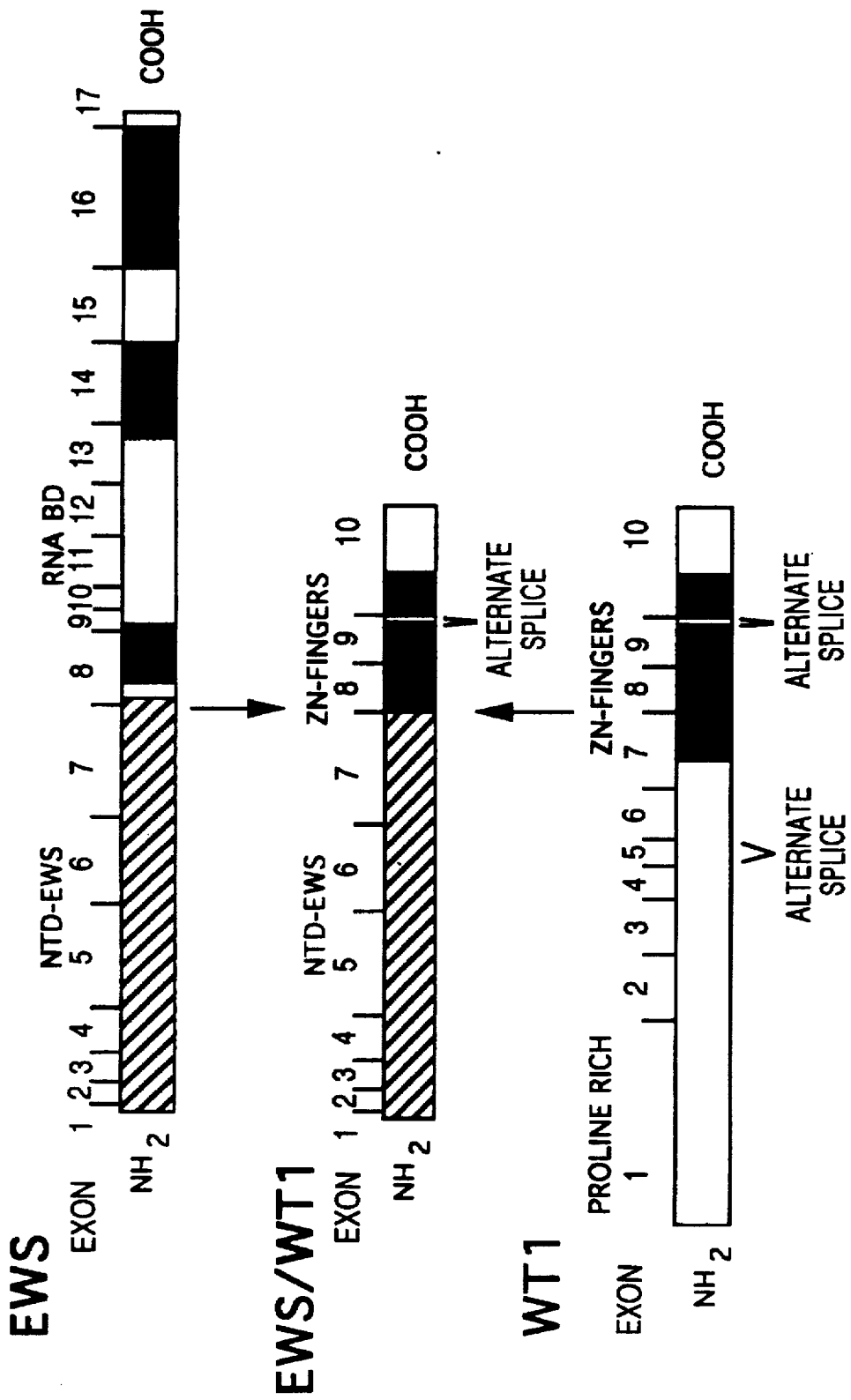
Figure 8A:
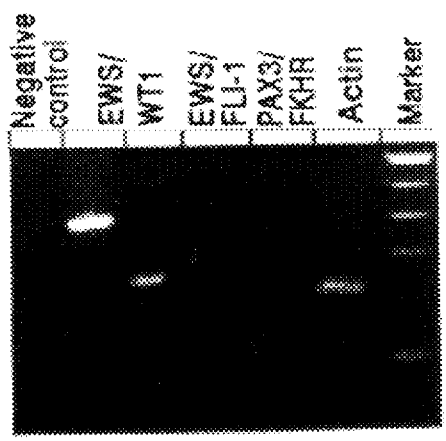
Figure 8B:
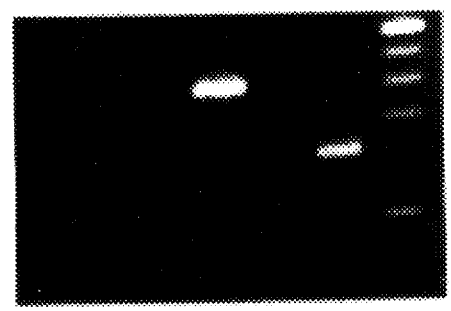
Figure 8C:
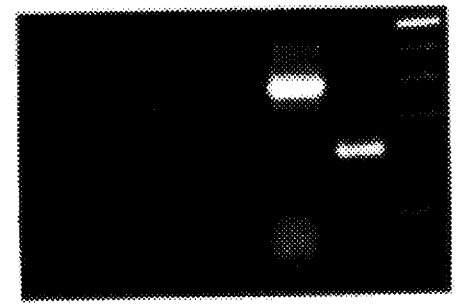
Figure 8D:
Figure 8E:
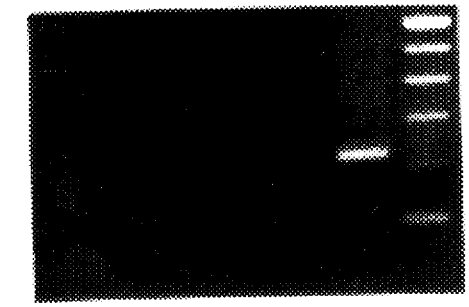

FIG. 7A is a schematic diagram of the deduced translation products of the wild type and chimeric transcripts. Vertical bars delineate the portions of the proteins encoded by different exons. Structural features are indicated. NTD-EWS, N-terminal domain of EWS. RNA BD, putative RNA binding domain. ZN fingers, zinc-finger DNA-binding domain.

FIG. 7B is a nucleotide sequence of the cDNA obtained by RT-PCR amplification of chimeric transcript (SEQUENCE ID NO. 19). The position of the junction between EWS and WT1 is indicated.

Figure 9:
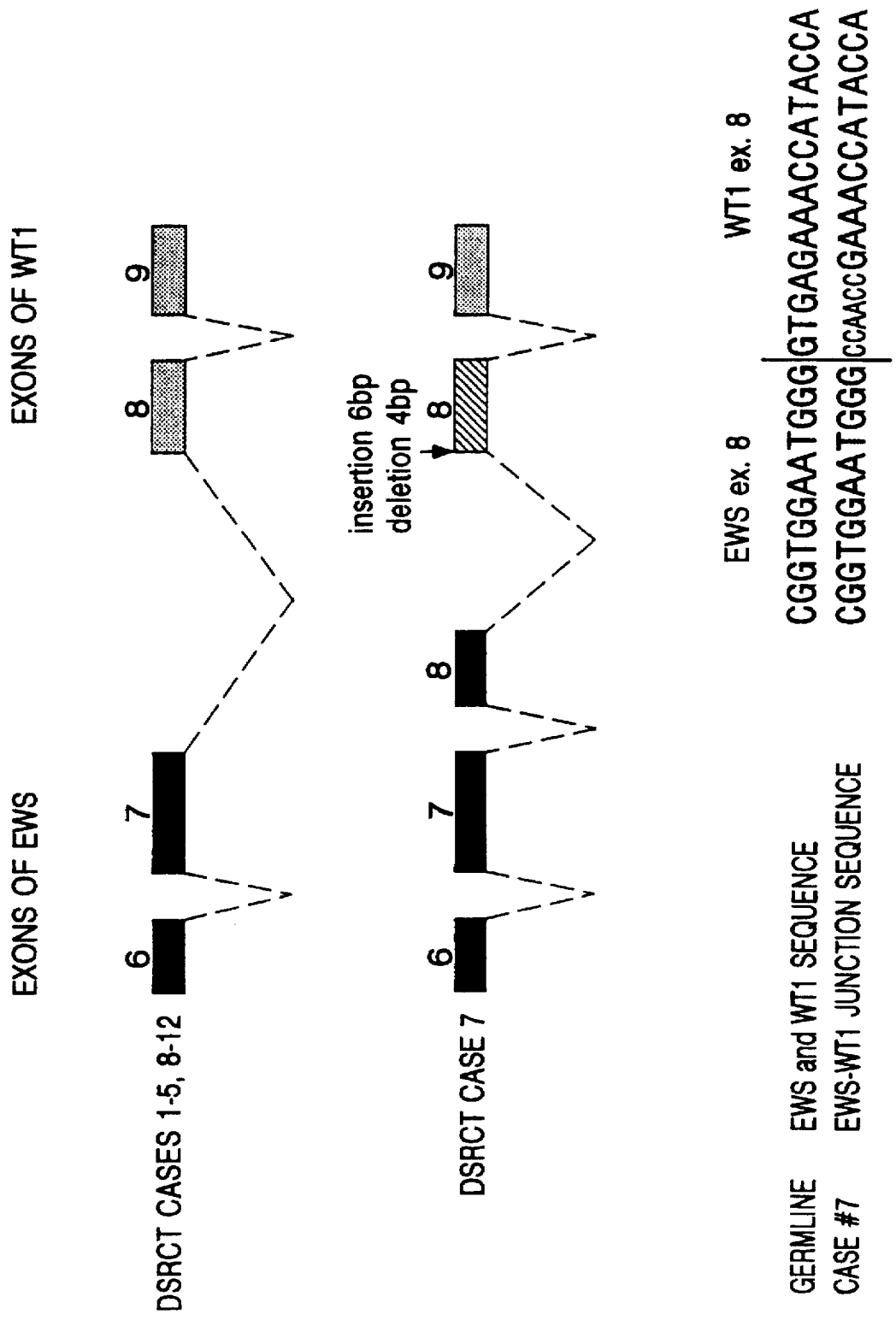

FIG. 8A, 8B, 8C, 8D, and 8E are RT-PCR performed using a panel with three different pairs of primers (rows) on desmoplastic small round cell tumor (A), Ewing sarcoma (B), alveolar rhabdomyosarcoma (C), embryonal rhabdomyosarcoma (D), and Wilms tumor (E). Results with two cases of desmoplastic small round cell tumor are shown (A); a case carrying a usual chimeric transcript displays a 268 bp band (lane#3), while the size of the band in the case with a variant chimeric transcript is 451 bp (lane #2). FIG. 9 is a diagram of the junction region of EWS-WT1 chimeric transcripts. Black boxes indicate EWS exons. Stripped boxes indicate WT1 exons. Numbers above boxes indicate the exon number of each gene. The chimeric transcript is composed of the first seven exons of EWS linked to the last three exons of WT1 (top), except in one case, where EWS exon 8 is also present (middle). Sequence of the EWS-WT1 chimeric transcript junction for the variant case (case 7, EXAMPLE 3) is shown at the bottom.

DETAILED DESCRIPTION OF THE INVENTION

Throughout this application, the following standard abbreviations are used to indicate specific nucleotides:

| | |
|---|---|
| C = cytosine | A = adenosine |
| T = thymidine | G = guanosine |

The present invention provides an isolated nucleic acid molecule encoding a chimeric EWS-WT1 protein. As used herein, the term "isolated nucleic acid molecule" means a nucleic acid molecule that is, a molecule in a form which does not occur in nature. The term "chimeric EWS-WT1 protein" is used herein to mean a protein comprised of parts of EWS and WT1 proteins. Examples of a nucleic acid molecule are an RNA, cDNA, or isolated genomic DNA molecule encoding a chimeric EWS-WT1 protein. One non-limiting example of isolating a nucleic acid encoding a chimeric EWS-WT1 protein is to probe using methods well known in the art a genomic library with a natural or artificially designed DNA probe, which specifically hybridizes with the chimeric EWS-WT1 junction.

This invention further provides a cDNA molecule encoding a human EWS-WT1 chimeric protein having a coding sequence substantially the same as the coding sequence shown in SEQUENECE ID NO.18.

This invention provides a vector comprising an isolated nucleic acid molecule such as DNA, RNA, or cDNA encoding a chimeric EWS-WT1 protein. Examples of vectors are viruses such as bacteriophages (e.g. phage lambda), cosmids, plasmids, and other recombination vectors. Nucleic acid molecules are inserted into vector genomes by methods well known in the art. For example, insert and vector DNA can both be exposed to a restriction enzyme to create complementary ends on both molecules which base pair with each other and are then ligated together with a ligase. Alternatively, linkers can be ligated to the insert DNA which correspond to a restriction site in the vector DNA, which is then digested with the restriction enzyme which cuts at that site.

This invention also provides vectors comprising a DNA molecule encoding a chimeric EWS-WT1 protein, adapted for expression in a bacterial cell, an insect cell, a yeast cell, or a mammalian cell which additionally comprise the regulatory elements necessary for expression of the DNA in the bacterial, yeast, or mammalian cells so located relative to the DNA encoding a chimeric EWS-WT1 protein as to permit expression thereof. DNA having coding sequences substantially the same as the coding sequence shown in SEQUENCE ID NO. 18 may usefully be inserted into the vectors to express chimeric EWS-WT1 protein. Regulatory elements required for expression include promoter sequences to bind RNA polymerase and transcription initiation sequences for ribosome binding. As a non-limiting example, a bacterial expression vector includes a promoter such as the lac promoter and for transcription initiation the Shine-Dalgrano sequence and the start codon AUG (Maniatis et al., Molecular Cloning, Cold Spring Harbor Laboratory, 1982). Similarly, a eukaryotic expression vector includes a heterologous or homologous promoter for RNA polymerase II, a downstream polyadenylation signal, the start codon AUG, and a termination codon for detachment of the ribosome. Such vectors may be obtained commercially or assembled from the sequences described by methods well known in the art, for example the methods described above for constructing vectors in general. Expression vectors are useful to produce cells that express the chimeric EWS-WT1 protein.

This invention provides a nucleic acid probe comprising a nucleic acid molecule capable of specifically hybridizing with a unique sequence included within a sequence spanning a chimeric junction of the nucleic acid molecule encoding a chimeric EWS-WT1 protein, which sequence is not present in nucleic acid molecules encoding either EWS or WT1 proteins. As used herein, the phrase "specifically hybridizing" means the ability of a nucleic acid molecule to recognize a nucleic acid sequence complementary to its own and to form double-helical segments through hydrogen bonding between complementary base pairs. This invention also provides a nucleic acid probe wherein the nucleic acid is DNA or RNA. Nucleic acid probe technology is well known to those skilled in the art who will readily appreciate that such probes vary in length and may be labeled with a detectable label, such as a radioisotope or fluorescent dye, to facilitate detection of the probe. Detection of nucleic acid encoding a chimeric EWS-WT1 protein is useful as a diagnostic test for any disease process which is marked by its presence. DNA probe molecules are produced by insertion of a DNA molecule which encodes a chimeric EWS-WT1 protein or fragments thereof into suitable vectors, such as plasmids or bacteriophages, followed by insertion into suitable bacterial host cells and replication and harvesting of the DNA probes, all using methods well known in the art. As a non-limiting example, the DNA may be extracted from a cell lysate using phenol and ethanol, digested with restriction enzymes corresponding to the insertion sites of the DNA into the vector (discussed above), electrophoresed and cut out of then resulting gel. The probes are useful for 'in situ' hybridization or in order to locate tissues which express this nucleic acid. In addition, synthesized oligonucleotides (produced by DNA synthesizer) complementary to the sequence of a DNA molecule which encodes chimeric EWS-WT1 protein are useful as probes and for the use of amplification techniques such as the Polymerase Chain Reaction. Examples of such oligonucleotides are shown in SEQUENCE ID NO. 1 through SEQUENCE ID NO. 17.

This invention provides an antisense oligonucleotide having a sequence capable of binding specifically with any sequences of an mRNA molecule which encodes a chimeric EWS-WT1 protein so as to prevent translation of the mRNA molecule. The antisense oligonucleotide may have a sequence capable of binding specifically with any sequences of the cDNA molecule whose sequence is shown in ID SEQUENCE ID NO. 18. As used herein, the phrase "binding specifically" means the ability of a nucleic acid sequence to recognize a nucleic acid sequence complementary to its own and to form double-helical segments through hydrogen bonding between complementary base pairs. A particular example of an antisense oligonucleotide is an antisense oligonucleotide comprising chemical analogues of nucleotides.

This invention further provides an isolated protein which is a chimeric EWS-WT1 protein. As used herein, the term "isolated protein" means a protein molecule free of other cellular components. One example of such protein is an isolated human chimeric EWS-WT1 protein. An example of an isolated human chimeric EWS-WT1 protein is an isolated protein having substantially the same amino acid sequence as the amino acid sequence shown in SEQUENCE ID NO. 20. Another example of an isolated human chimeric EWS-WT1 protein is an isolated protein having substantially the same amino acid sequence as the amino acid sequence shown in SEQUENCE ID NO. 21. The amino acid sequences shown in SEQUENCE ID NO. 20 and SEQUENCE ID NO. 21 differ by three amino acids due to an mRNA alternative splice site. One means for obtaining isolated chimeric EWS-WT1 protein is to express DNA encoding the chimeric protein in a suitable host, using methods well known in the art. The chimeric protein may also be isolated from cells which express it, in particular from cells which have been transfected with the expression vectors described previously.

This invention also provides a method of diagnosing a desmoplastic small round cell tumor in a subject which comprises detecting in a sample from the subject a nucleic acid molecule encoding a chimeric EWS-WT1 protein, positive detection indicating the presence of desmoplastic small round cell tumor.

This invention further provides a method for detecting the nucleic acid molecule encoding the chimeric EWS-WT1 protein by size fractionation such as a polyacrylamide or an agarose gel.

This invention also provides a method for the detection of the nucleic acid molecule encoding the chimeric EWS-WT1 protein which comprises contacting the nucleic acid molecule from the sample with an EWS, WT1 or a chimeric EWS-WT1 probe capable of hybridizing with the nucleic acid molecule encoding the chimeric EWS-WT1 protein, wherein the probe is labeled with a detectable marker under conditions permitting the EWS, WT1 or the chimeric EWS-WT1 probe to hybridize with the nucleic acid molecule encoding the chimeric EWS-WT1 protein, thereby detecting the nucleic acid molecule encoding the chimeric EWS-WT1 protein. The detectable marker may be a radiolabeled molecule, a fluorescent molecule, an enzyme, or a ligand. In one possible means of performing this method, nucleic acids are extracted by precipitation from lysed cells and the mRNA is isolated from the extract using a column which binds the poly-A tails of the mRNA molecules. The mRNA is then exposed to radioactively labelled probe on a nitrocellulose membrane, and the probe hybridizes to and thereby labels complementary mRNA sequences. Binding may be detected by autoradiography or scintillation counting. However, other methods for performing these steps are well known to those skilled in the art, and the discussion above is merely an example.

This invention provides a method for the detection of the nucleic acid molecule encoding the chimeric EWS-WT1 protein which comprises amplifying the nucleic acid molecule encoding the chimeric EWS-WT1 protein, thereby detecting the nucleic acid molecule encoding the chimeric EWS-WT1 protein.

This invention also provides method for the amplification of the nucleic acid molecule encoding the chimeric EWS-WT1 protein which comprises contacting the nucleic acid molecule from the sample with at least two primers bracketing a translocation breakpoint of a t(11;22) (p13;q12) translocation under conditions for polymerase chain reaction. The amplified nucleic acid molecule encoding the chimeric EWS-WT1 protein may be detected by size fractionation such as a polyacrylamide or an agarose gel.

This invention also provides a method for the detection of the amplified nucleic acid molecule encoding the chimeric EWS-WT1 protein which comprises contacting the amplified nucleic acid molecule encoding the chimeric EWS-WT1 protein with an EWS, WT1, or a chimeric EWS-WT1 probe capable of hybridizing with the nucleic acid molecule encoding the chimeric EWS-WT1 protein, wherein the probe is labeled with a detectable marker under conditions permitting the EWS, WT1, or the chimeric EWS-WT1 probe to hybridize with the amplified nucleic acid molecule encoding the chimeric EWS-WT1 protein, detecting hybridization of the amplified nucleic acid molecule encoding the chimeric EWS-WT1 protein with the probe, thereby detecting the amplified nucleic acid molecule encoding the chimeric EWS-WT1 protein. The detectable marker may be a radiolabeled molecule, a fluorescent molecule, an enzyme, or a ligand.

This invention further provides a method of diagnosing a desmoplastic small round cell tumor in a subject which comprises detecting in a sample from the subject a chimeric EWS-WT1 protein, positive detection indicating the presence of desmoplastic small round cell tumor. The chimeric EWS-WT1 protein may be detected by size fractionation using western blotting or by immunoprecipitation using methods well known in the art.

This invention provides an antibody directed to the chimeric EWS-WT1 protein, for example a monoclonal antibody directed to an epitope that spans the junction region of the above-mentioned chimeric protein. For example, monoclonal antibodies are prepared using hybridoma technology by fusing antibody producing B cells from immunized animals with myeloma cells and selecting the resulting hybridoma cell line producing the desired antibody. Alternatively, synthetic peptides may be prepared using commercially available machines and the amino acid sequence or parts of thereof spanning the junction region shown in FIG. 7A, and SEQUENCE ID NO. 20–21. As a still further alternative, DNA, such as a cDNA or a fragment thereof (SEQUENCE ID NO. 19), may be cloned and expressed and the resulting polypeptide recovered and used as an immunogen. These antibodies are useful to detect the presence of chimeric EWS-WT1 protein encoded by the isolated nucleic acid, or to inhibit the function of the chimeric protein in living animals, in humans, or in biological tissues or fluids isolated from animals or humans.

This invention also provides a method of inhibiting the growth of a neoplastic cell, wherein the cell is characterized by the presence of a chimeric EWS-WT1 protein which comprises contacting an antibody which specifically recognizes the chimeric EWS-WT1 fusion protein under suitable conditions so that an antibody-antigen complex is formed, thereby inhibiting the growth of the neoplastic cell. The neoplastic cell may be a desmoplastic small round cell tumor. As a non-limiting example, the desmoplastic small round cell tumor is located in the abdominal cavity or in the thorax.

This invention further provides a method of inhibiting the growth of a neoplastic cell wherein the cell is characterized by the presence of a chimeric EWS-WT1 protein which comprises contacting an antibody conjugated to a therapeutic agent, wherein the antibody recognizes the chimeric EWS-WT1 protein under suitable conditions so that an antibody-antigen complex is formed, thereby inhibiting the growth of the neoplastic cell. The neoplastic cell may be a desmoplastic small round cell tumor. As a non-limiting example, the desmoplastic small round cell tumor is located in the abdominal cavity or in the thorax. The therapeutic agent may be selected from the group consisting of radioisotopes, cytotoxic compounds, toxins, bacterial toxins, toxoids, and chemotherapeutic agents.

This invention provides a method of inhibiting the growth of a neoplastic cell wherein the cell is characterized by the presence of a chimeric EWS-WT1 DNA which comprises contacting a DNA-binding peptide, wherein the DNA binding peptide specifically recognizes a unique junction region of the chimeric EWS-WT1 DNA under suitable conditions so that a DNA-binding peptide-chimeric EWS-WT1 DNA complex is formed, thereby inhibiting the growth of the neoplastic cell. The neoplastic cell may be a desmoplastic small round cell tumor. As a non-limiting example, the desmoplastic small round cell tumor is located in the abdominal cavity or in the thorax.

This invention provides a method of inhibiting the growth of a neoplastic cell wherein the cell is characterized by the presence of a chimeric EWS-WT1 DNA which comprises contacting a DNA-binding peptide conjugated to a therapeutic agent, wherein the DNA binding peptide specifically recognizes a unique junction region of the chimeric EWS-WT1 DNA under suitable conditions so that a DNA-binding peptide-chimeric EWS-WT1 DNA complex is formed, thereby inhibiting the growth of the neoplastic cell. As a non-limiting example, the desmoplastic small round cell tumor is located in the abdominal cavity or in the thorax. The therapeutic agent may be selected from the group consisting of radioisotopes, cytotoxic compounds, toxins, bacterial toxins, toxoids, and chemotherapeutic agents.

Antisense oligonucleotides drugs inhibit translation of mRNA encoding the chimeric EWS-WT1 protein. Synthetic oligonucleotides, or other antisense chemical structures are designed to bind to mRNA encoding the chimeric EWS-WT1 protein and inhibit translation of mRNA and are useful as drugs to inhibit expression of chimeric EWS-WT1 gene in patients. This invention provides a means to therapeutically alter levels of expression of chimeric EWS-WT1 protein by the use of a synthetic antisense oligonucleotide drug (SAOD) which inhibits translation of mRNA encoding this chimeric protein. Synthetic oligonucleotides, or other antisense chemical structures designed to recognize and selectively bind to mRNA, are constructed to be complementary to portions of the nucleotide sequence (ID SEQUENCE NO. 19) that spans the junction region of the EWS and WT1 genes, RNA or of chemically modified, artificial nucleic acids. The SAOD is designed to be stable in the blood stream for administration to patients by injection, or in laboratory cell culture conditions, for administration to cells removed from the patient. The SAOD is designed to be capable of passing through cell membrane in order to enter the cytoplasm of the cell by virtue of physical and chemical properties of the SAOD which render it capable of passing through cell membrane (e.g. by designing small, hydrophobic SAOD chemical structures) or by virtue of specific transport systems in the cell which recognize and transport the SAOD into the cell. In addition, the SAOD can be designed for administration only to certain selected cell populations by targeting the SAOD to be recognized by specific cellular uptake mechanisms which bind and take up the SAOD only within certain selected cell populations. For example, the SAOD may be designed to bind to a receptor found only in certain cell types, as discussed above. The SAOD is also designed to recognize and selectively bind to the target mRNA sequence by virtue of complementary base pairing to the mRNA. Finally the SAOD is designed to inactivate the target mRNA sequence by any of three mechanisms: 1) by binding to the target mRNA and thus inducing degradation of the mRNA by intrinsic cellular mechanisms such as RNAse I digestion, 2) by inhibiting translation of the mRNA target by interfering with the binding of translation-regulating factors or ribosomes, or 3) by inclusion of other chemical structures, such as ribozyme sequences or reactive chemical groups, which either degrade or chemically modify the target mRNA. Synthetic antisense oligonucleotide drugs have been shown to be capable of the properties described above when directed against mRNA targets (Cohen, 1989; and Weintraub, 1990). In addition, coupling of ribozymes to antisense oligonucleotides is a promising strategy for inactivating target mRNA (Lange et al., 1994). An SAOD serves as an effective therapeutic agent if it is designed to be administered to a patient by injection, or if the patient's target cells are removed, treated with the SAOD in the laboratory, and replaced in the patient. In this manner, an SAOD serves as a therapy to reduce gene expression in particular target cells of a patient, in any clinical condition which may benefit from reduced expression of chimeric EWS-WT1 protein.

This invention provides a method of inhibiting the growth of a neoplastic cell wherein the cell is characterized by the presence of a chimeric EWS-WT1 mRNA which comprises contacting an antisense nucleic acid molecule, wherein the antisense nucleic acid molecule recognizes a unique junction region of the chimeric EWS-WT1 mRNA under suitable conditions so that an antisense nucleic acid-chimeric EWS-WT1 mRNA complex is formed, thereby blocking translation of the chimeric EWS-WT1 mRNA and inhibiting the growth of the neoplastic cell. As a non-limiting example, the desmoplastic small round cell tumor is located in the abdominal cavity or in the thorax.

This invention also provides a method of inhibiting the growth of a neoplastic cell wherein the cell is characterized by the presence of a chimeric EWS-WT1 mRNA which comprises contacting a ribozyme molecule, wherein the ribozyme molecule specifically recognizes a unique junction region of the chimeric EWS-WT1 mRNA under suitable conditions so that a ribozyme-chimeric EWS-WT1 mRNA complex is formed, thereby cleaving the chimeric EWS-WT1 mRNA and inhibiting the growth of the neoplastic cell. As a non-limiting example, the desmoplastic small round cell tumor is located in the abdominal cavity or in the thorax.

This invention will be better understood from the Experimental Details which follow. However, one skilled in the art will readily appreciate that the specific methods and results discussed are merely illustrative of the invention as described more fully in the claims which follow thereafter.

Experimental Details

Tissue Samples—EXAMPLE 1

Frozen tissue or extracted DNA was available in five cases of histologically typical DSRCT. Routine histopathology and immunohistochemical analysis were performed at the time of initial diagnosis as described elsewhere (Gerald et al., 1991). All five cases showed evidence of multiphenotypic differentiation with expression of neural, myogenic, and epithelial lineage markers. Brief clinical and pathologic descriptions follow.

Case 1 was 16 year old male who presented with pain and an abdominal mass. He was found to have multiple tumors involving the omentum, colon, and pelvis. The tissue studied was obtained from a resection of residual tumor following chemotherapy. The histologic appearance of the tumor was characteristic of DSRCT, and immunohistochemical studies showed expression of neural, myogenic, and epithelial markers in the tumor. Case 2 was a 26 year old male who presented with low back pain of two months duration and a left upper quadrant mass. Imaging studies revealed widespread tumor in lungs, liver, pelvis, and mesentery. The tissue studied was obtained from a diagnostic needle aspiration biopsy. Pathologic examination showed a typical DSRCT with myogenic and epithelial differentiation demonstrated by immunohistochemical studies. The clinical and pathologic details in Case 3 have been previously reported and illustrated (case 2 in Rodriguez et al., 1993). Morphologically, this was a classic DSRCT in a 32 year old male, and the tumor reacted with antibodies to keratin, desmin, and S100 protein. Case 4 was a 17 year old female who presented with difficulty swallowing. She was found to have a posterior mediastinal tumor encasing the pleura, the hilum of left lower lobe of lung, and pericardium. The tumor was biopsied and histopathology showed isolated clusters of DSRCT within normal fibroadipose tissue. Immunohistochemical studies revealed expression of neural and myogenic antigens in the tumor cells. Case 5 was 24 year old male who presented with headaches, vomiting, vertigo, and hearing loss, and was found to have meningeal-based intracranial mass. Imaging studies showed no evidence of intraabdominal pathology. Histopathology of the resected tumor showed a typical DSRCT, with immunoreactivity for keratin and desmin.

DNA Extraction and Blot analysis—EXAMPLE 1

Genomic DNA was extracted from snap-frozen tissues by a standard manual organic extraction protocol (Sambrook et al., 1989) or on an automated DNA extractor (Model 340A, Applied Biosystems, Foster City, Calif.) following the manufacturer's protocols. Total RNA was extracted by a modified Chomczynski method (Chomczynski and Sacchi, 1987). Southern blots of genomic DNA digested with EcoRI or HindIII were hybridized overnight with probes radiolabelled to a high specific activity by random priming. The hybridized filters were washed at high stringency and filmed for 1 to 4 days. Placental DNA was used as germline, i.e. normal, control. For Northern blotting, approximately 10 μg of total RNA were electrophoresed in a 1% agarose/2.2M formaldehyde gel (Sambrook et al., 1989). The gel was stained with ethidium bromide for visualization of RNA, and then destained prior to capillary transfer.

For the EWS gene, a 741 base pair (bp) partial complementary DNA (cDNA) probe generated by PCR, as previously described (Ladanyi et al., 1993), was used. This probe corresponds to nucleotides 527 to 1267 of the EWS cDNA and includes exons 7 to 11, which constitute the genomic EWS breakpoint cluster region in ES/PNET (Delattre et al., 1992; and Plougastel et al., 1993). Previously, this probe was shown to detect EWS rearrangement in 87% of unselected cases of ES or PNET, including all cases with a typical or complex t11;22)(q24;q12) (Ladanyi et al., 1993). Southern and northern blot filters were also rehybridized with a 1.8 kb EcoRI fragment of WT33, a WT1 cDNA (Call et al., 1990). This WT1 probe hybridizes to all 10 exons of the WT1 gene; almost all EcoRI and HindIII-digested genomic fragments of WT1 are detected, except for a portion of the relatively large fifth intron (Haber et al., 1991; and Gessler et al., 1992).

RT-PCR—EXAMPLE 1

RT-PCR was performed on total RNA, using the GeneAmp RNA PCR kit (Perkin-Elmer, Norwalk, Conn.), according to the recommended protocol, on an automated thermal cycler (Omnigene; Hybaid, UK). Reverse transcription was performed for 30 min at 42° C. on 1 μg of total RNA, using random hexamers. The reverse transcriptase is inactivated at 99° C. for 5 min. The PCR reagents were then added. The final MgCl$_2$ concentration was 1.75 mM, and the amount of each primer was 30 pmol/reaction. The cycling parameters were: 40 cycles of 940 for 1 min, 60° for 1 min, 72° for 30 sec, followed by a final extension at 72° for 5 min.

The forward primer for EWS exon 7 was 5'-TCCTACAGCCAAGCTCCAAGTC-3' (SEQUENCE ID NO. 1, primer 22.3 in Delattre et al., 1992). The reverse primers for WT1 exons 8 and 9 were 5'-ACCTTCGTTCACAGTCCTTG-3' (SEQUENCE ID NO. 16) and 5'-GACCAGGAGAACTTTCGCTGAC-3' (SEQUENCE ID NO. 17), respectively.

Tissue Samples and General Methods—EXAMPLE 2

Established clinical, histologic and immunohistochemical criteria were used for diagnosis in each case (Gerald et al., 1993). Tumor and normal tissue samples were collected at the time of surgery and immediately frozen in liquid nitrogen. Table 1 shows the main clinical features of the six patients with DSRCT and the karyotypes of the two tumors studied cytogenetically. Southern blots were performed using Zetaprobe nylon membrane (Biorad, Richmond, Calif.) according to the manufacturer's directions. Oligonucleotides used as primers for sequencing and RT-PCR are listed in Table 2.

Size Selected Genomic Library Construction and Screening—EXAMPLE 2

One hundred micrograms of DNA isolated from frozen tumor (DSRCT case 3) was subjected to complete digestion with BamHI (Promega, Madison, Wis.). Following phenol-chloroform extraction the entire sample was loaded on a 0.8% preparative agarose gel, electrophoresed with appropriate size markers (1 kb ladder, Gibco-BRL, Gaithersburg, Md.) and visualized by low intensity UV transillumination of the ethidium bromide stained gel. The region of the gel containing DNA fragments migrating in the 6 to 7 kb size range was excised and the DNA isolated using silica gel matrix (Qiagen, Chatsworth, Calif.). One hundred-fifty ng of

TABLE 1

Main clinical features of the six cases of DSRCT in EXAMPLE 2.

| Case | Sex | Age, yr. | Primary site |
|---|---|---|---|
| 1 | M | 15 | abdomen |
| 2 | F | 17 | chest |
| 3 | M | 16 | abdomen |
| 4 | M | 10 | abdomen |
| 5 | M | 34 | abdomen |
| 6 | M | 32 | abdomen |

Karyotype (Rodriguez et al., 1993): Case 5: 49–92, <4n>,XXYY,–1,del(1)(p34),–8,–11,–17,–18,–19,+mar[cp5]/46,XY[6]. In addition, one cell each showed a del(22)(q12) and a del(11)(p13). Case 6: 46–50,XY,+5,t(11;22)(p13;q11.2),+18[cp10].

TABLE 2

DNA oligonucleotides used in RT-PCR and Sequencing

| Designation | Gene/exon or intron | SEQUENCE ID NO. | Sequence |
|---|---|---|---|
| EWS-22.3 | EWS/exon 7 | 1 | 5'-TCCTACAGCCAAGCTCCAAGTC-3' |
| EWS-8.1 | EWS/exon 8 | 2 | 5'-GCATGAGTGGCCCTGATAAC-3' |
| EWS-8.2 | EWS/exon 8 | 3 | 5'-ATTCCACCGCGTCCTCCTCC-3' |
| WT1-10.1 | WT1/exon 10 | 4 | 5'-GCCACCGACAGCTGAAGGGC-3' |
| WT1-10.2 | WT1/exon 10 | 5 | 5'-GACACTGAACGGTCCCCGA-3' |
| WT1-7.1 | WT1/3'intron-exon 7 junction | 6 | 5'-CTTACCAGTGTGCTTCCTGC-3' |
| WT1-7.2 | WT1/intron 5' to exon 7 | 7 | 5'-CTTCCTCTTACTCTCTGCCTGC-3' |
| WT1-EWS 1.0 | EWS/exon 8 | 8 | 5'-GTTATCAGGGCCACTCATGC-3' |
| WT1-EWS 2.0 | WT1/exon 7 | 9 | 5'-CATCTGAGACCAGTGAGAAACG-3' |
| WT1 +KTS | WT1/junction exons 9 and 10 | 10 | 5'-AAGGGCTTTTCACTTGTTTTAC-3' |
| WT1 –KTS | WT1/junction exons 9 and 10 | 11 | 5'-AAGGGCTTTTCACCTGTATGAG-3' | purified size-selected DNA was ligated to lambda ZAP Express BamH I vector arms (Stratagene, La Jolla, Calif.) and packaged with Gigapack II Gold (Stratagene, La Jolla, Calif.) packaging extract. A portion of the unamplified library was plated at high density and screened using $^{32}$P-labeled EWS probe as described (Gerald et al., 1986). Positive clones were purified by low density screening and recombinant fragmentsisolated from phage stocks.

RT-PCR—EXAMPLE 2

RT-PCR detection of transcripts was performed using 1 microgram of total RNA as starting material and a GeneAmp RNA-PCR kit (Perkin-Elmer, Branchburg, N.J.) according to the manufacturer's recommendations. Random hexamers or transcript specific oligonucleotide primers (Table 2) were used for cDNA synthesis. PCR was performed with an initial denaturation step of 95° C. for 2 minutes followed by thirty-five cycles consisting of denaturation at 94° C. for 30 s, annealing at 65° C. for 30 s and extension at 72° C. for 30 s with extension for five minutes in the last cycle. Products were identified by gel electrophoresis using 2% agarose and ethidium bromide staining.

Cloning and Sequencing of PCR products—EXAMPLE 2

PCR products were isolated from 2% agarose gels. Purified products were ligated into Hind II-digested phosphatase-treated pUC18. Direct sequencing of purified recombinant plasmid DNA was carried out by PCR using the Circumvent kit (New England Biolabs, Beverly, Mass.), $^{35}$S-dATP (800 Ci/mM, Dupont-New England Nuclear, Boston, Mass.) and the forward and reverse sequencing primers for pUC18 (Promega, Madison, Wis.) or exon specific primers (Table 2). Products were analyzed on 6 or 8% polyacrylamide-urea sequencing gels. Sequences were analyzed using GeneWorks Version 2.0 Sequence Analysis software.

Characteristics of the Tumors Analyzed—EXAMPLE 3

Study cases included 12 DSRCT (9 males and 3 females; mean age 19 yr.; range 11–32 yr. ). In eleven patients the tumor involved the abdominal cavity and in one patient it involved the pleura and posterior mediastinum. The diagnosis was based on established histopathological and immunohistochemical criteria (Gerald et al., 1991).

initial denaturation step of 95° C. for 2 minutes, followed by 35 cycles including a denaturation step at 94° C. for 30 s, annealing at 65° C. for 30 s, and extension at 72° C. for 60 s, with 6 minutes of extension after the completion of the last cycle. Products were identified by 2% agarose gel electrophoresis and ethidium bromide staining.

Primer Selection—EXAMPLE 3

Oligonucleotide primer pairs, used to amplify the chimeric transcripts of alveolar rhabdomyosarcoma, Ewing's sarcoma/PNET, and DSRCT have been described (Delattre et al., 1992; Galili et al., 1993; Davis et al., 1994), and are listed in Table 3.

The quality of the extracted RNA was assessed by RT-PCR using random hexamers and β-actin primers (Clontech). RNA samples prepared from normal liver, kidney, and spleen were used as non-neoplastic controls in all procedures.

Cloning and sequencing—EXAMPLE 3

Products of RT-PCR were isolated from 2% agarose gels using silicagel matrix (QIAGEN, Chatsworth, Calif.), and ligated into pUC18. Direct sequencing of purified recombinant plasmid DNA was done by a modified Sanger method (Sanger et al., 1977) using the Circumvent® kit (New England biolabs, Beverly, Mass.), 3$^{35}$S-dATP (800 Ci/mM, New England Nuclear), and forward and reverse sequencing primers for pUC18 (Promega) or exon specific primers (Table 3). Products were evaluated on 6–8% polyacrylamide-urea sequencing gels. Sequences were

TABLE 3

Primers and sequences used in the RT-PCR assays.

| Designation | Gene/exon or intron | SEQUENCE ID NO. | Sequence |
|---|---|---|---|
| WT1-10.2 | WT1/exon 10 | 5 | 5'-GACACTGAACGGTCCCCGA-3' |
| WT1-10.1 | WT1/exon 10 | 4 | 5'-GCCACCGACAGCTGAAGGGC-3' |
| EWS 22.3 | EWS/exon 7 | 1 | 5'-TCCTACAGCCAAGCTCCAAGTC-3' |
| EWS-8.1 | EWS/exon 8 | 2 | 5'-GCATGAGTGGCCCTGATAAC-3' |
| FLI-1 11.3 | FLI-1/exon 11 | 12 | 5'-ACTCCCCGTTGGTCCCCTCC-3' |
| 5'-PAX3 | PAX3 | 13 | 5'-GCACTGTACACCAAAGCACG-3' |
| 5'-PAX7 | PAX7 | 14 | 5-TTTGAGAGGACCCACTACCC-3' |
| 3'-FKHR | FKHR | 15 | 5'-AACTGTGATCCAGGGCTGTC-3' |

The remaining 49 tumors included: 22 rhabdomyosarcomas (15 males and 7 females; mean age 17.9 yr.; range 2–47 yr.; 13 alveolar and 9 embryonal (Tsokos, 1994)); 17 Wilms' tumors (10 males and 6 females; mean age, 4.6 yr.; range 1–19 yr.); eight Ewing's sarcomas of bone (5 females, 3 males; mean age 21.6 yr.; range 17–31 yr.; 7 of them showing involvement of soft tissues), and 2 PNET (1 male, 1 female, both 31 years old; one in a paraspinal location, and the other in the femur).

Sample Collection—EXAMPLE 3

Tumor and normal tissue samples were collected at the time of surgery and immediately frozen in liquid nitrogen. RNA extraction was performed by standard procedures (Chomczynski and Sacchi, 1987).

RT-PCR EXAMPLE 3

RT-PCR detection of transcripts was performed using 1 μg of total RNA as template, and a GeneAmpr RNA-PCR kit (Perkin-Elmer, Roche Molecular Systems, Branchburg, N.J.) following the recommendations of the manufacturer. Reverse transcription included an incubation period of 45 minutes at 42° C., with random hexamers or transcript-specific primers, followed by a 5-minute period at 99° C. to denature the enzyme. PCR was then performed with an analyzed using GeneWorks® version 2.0 (Intelligenetics, Inc.).

EXAMPLE 1

Non-germline bands were identified in multiple enzyme digests on Southern blots probed with EWS in cases 1, 2, 3, and 5, but not in case 4 (FIG. 1). Southern blot analysis of the WT1 gene was performed in four cases (cases 1, 3, 4, and 5) and revealed non-germline bands in cases 1, 3, and 5 (FIG. 2). In all three cases, one or more of the rearranged WT1 bands co-migrated with rearranged EWS bands in both enzyme digests (FIG. 2), indicating the presence of a rearrangement between the EWS and WT1 genes. Karyotypic data in case 3 have been previously reported (Rodriguez et al., 1993). Cytogenetic analysis was not performed on the other four cases.

High molecular weight RNA was obtained only in case 3. Northern blotting in this case showed a broad EWS band, suggestive of an aberrant transcript of slightly larger size (approximately 2.5 kb) than the expected 2 kb EWS transcript (FIG. 3). Rehybridization with a WT1 probe showed a single abnormally sized transcript in case 3, apparently comigrating with the aberrant EWS transcript. The normal 3 kb WT1 transcript was seen in the cell line K562. The finding in case 3 of aberrant EWS and WT1 transcripts of the same size suggested the presence of a chimeric mRNA resulting from the putative translocation between the EWS and WT1 genes.

RT-PCR using an EWS exon 7 primer and WT1 exon 8 or 9 primers in cases 1 and 3 revealed identical single PCR products consistent in size with a junction of EWS exon 7 to WT1 exon 8 in both cases (FIG. 4). Sequencing of the PCR product in case 3 showed an in-frame fusion of EWS exon 7 to WT1 exon 85. No RNA and no tissue for RNA extraction were available in cases 2, 4, and 5.

The unique features of DSRCT suggest that it represents a novel, distinct neoplastic entity. Predilection for young adults, especially males, frequent serosal abdominal involvement, prominent desmoplastic response, and the presence of multi-lineage differentiation, as demonstrated by immunohistochemistry, are helpful in establishing the diagnosis (Gerald et al., 1991). Its histologic and clinical attributes do, however, overlap with other primitive tumor types, including ES, PNET, rhadomyosarcoma, rhabdoid tumor, and Wilms' tumor. The precise nosologic position and cell of origin of DSRCT remain controversial and its molecular pathogenesis is completely unknown. The concept of DSRCT as an entity has recently been strengthened by the identification of a specific recurrent chromosomal abnormality. Cytogenetic data have been published in 5 cases of DSRCT (Sawyer et al., 1992; Shen et al., 1992; Biegel et al., 1993 and Rodriguez et al., 1993). The "classic" translocation in DSRCT appears to be t11;22)(p13;q12), seen in 3 cases (Sawyer et al., 1992; Biegel et al., 1993 and Rodriguez et al., 1993). A fourth case showed a "variant" t(2;21;22) (Shen et al., 1992), and the last case (case 3 in EXAMPLE 1) contained one cell with del(22q12) and one cell with del(11p13) (Rodriguez et al., 1993).

Chromosome band 22q12 is the site of the EWS gene. This gene is involved in three sarcoma-associated translocations, t11;22)(q24;q12) and t(21;22)(q22;q12) in ES, and t(12;22)(q13;q12) in CCS (Delattre et al., 1992; Zucman et al., 1993 and Sorensen et al., 1994). Indeed, EWS was first identified by the cloning of the ES translocation; its normal function remains unclear, although one portion appears to encode an RNA binding domain (Delattre et al., 1992). The 11q24 and 21q22 breakpoints in the ES translocations lie respectively within the FLI1 and ERG genes, members of the ETS family of transcription factors (Delattre et al., 1992 and Sorensen et al., 1994). The 12q13 breakpoint in CCS involves another transcription factor gene, ATF-1 (Zucman et al., 1993). In all three translocations, the sequence-specific DNA binding domain encoded by a transcription factor gene is juxtaposed to putative regulatory elements in the proximal portion of the EWS gene, replacing the proposed RNA binding domain of the latter (Delattre et al., 1992; Zucman et al., 1993 and Sorensen et al., 1994). The 22q12 breakpoints in ES/PNET are clustered in a 7 kb segment of genomic DNA, between exons 7 and 11 of EWS (Plougastel et al., 1993 and Zucman et al., 1992). The breakpoints in the two cases of CCS analyzed so far were located in the same region of the EWS gene (Zucman et al., 1993). Using an EWS cDNA probe that spans the breakpoint cluster region, EWS rearrangement was detected in 4 of 5 cases of DSRCT. The negative result in case 4 may have been due to insufficient tumor in the sample submitted for molecular analysis. Indeed, histopathologic examination of the remainder of the resected tissue in this case showed only isolated nests of tumor.

Karyotypic information was only available in case 3 of the five cases in EXAMPLE 1. The clonal karyotype was near-tetraploid, and contained del (1) (p34), numerical abnormalities, and an unidentified marker chromosome (Rodriguez et al., 1993). However, the cytogenetic analysis also detected one cell with del(22) (q12) and one cell with del(11) (p13) (Rodriguez et al., 1993). Although none of the other cases studied were karyotyped, it was hypothesized that a t11;22) (p13;q12) may be present at least in the four rearranged cases, similar to the cytogenetic findings in 3 of 5 published cases. In case 3, this translocation may have been masked as the marker chromosome or present in cells that did not yield analyzable metaphases.

On the assumption that the structure of this translocation involving the EWS gene is similar to the translocations in ES/PNET and CCS, transcription factor genes localized to 11p13 were considered as candidate translocation partners in DSRCT. Putative or definite transcription factor genes mapped to 11p13 include the Wilms' tumor zinc-finger gene, WT1 (Call, et al., 1990), the aniridia paired box and homeobox gene, AN2/PAX6 (Ton et al., 1991), and TTG2/RHOM2, a LIM-domain gene involved in the t(11;14) (p13;q11) of T-cell acute lymphoblastic leukemia (Boehm et al., 1991; and Royer-Pokora et al., 1991). Wilms' tumor is a primitive renal tumor which may in some cases show heterologous differentiation, somewhat akin to the multi-lineage differentiation in DSRCT. The WT1 gene is expressed in early stages of renal differentiation and in blastemal-predominant Wilms' tumor (Gerald et al., 1992 and Yeger et al., 1992). For this reason, WT1 was considered a prime candidate translocation partner in 11p13.

Using a WT1 cDNA probe, rearranged bands were detected comigrating with the rearranged EWS bands in multiple enzyme digests in cases 1, 3, and 5. No WT1 rearrangement was detected in case 4, which also lacked a detectable EWS rearrangement, possibly because of insufficient viable tumor in the sample studied (see above). The demonstration of comigration of rearranged bands provides strong molecular evidence of a classic or complex t11;22) (p13;q12), resulting in a rearrangement between EWS and WT1. Furthermore, Northern blot analysis of case 3 showed aberrant EWS and WT1 transcripts of the same size (2.5 kb), suggesting the presence of a chimeric EWS-WT1 RNA species resulting from the translocation. EWS is ubiquitously expressed (Delattre et al., 1992); in contrast, WT1 expression is tissue- and developmental stage-specific (Call et al., 1990). The strong expression of a transcript hybridizing with a WT1 probe in DSRCT may thus be considered significant in itself; in addition, the transcript appears smaller than the known splice variants of WT1 (Haber et al., 1991). The other translocations involving EWS result in chimeric transcripts (Delattre et al., 1992; Zucman et al., 1993 and Sorensen et al., 1994). That the rearrangement between EWS and WT1 in DSRCT follows the same pattern was confirmed in at least two of our cases by RT-PCR using an EWS exon 7 primer and WT1 exon 8 or 9 primers which revealed a single PCR product of the same size in both cases. Sequencing of the PCR product showed an in-frame junction of EWS exon 7 to WT1 exon 85. Thus, this chimeric RNA encodes a putative protein in which the RNA-binding domain of EWS is replaced by the three carboxy terminal zinc fingers of the WT1 DNA-binding domain. The structural consequences of this translocation therefore appear similar to the other translocations involving EWS (Delattre et al., 1992; Zucman et al., 1993 and Sorensen et al., 1994).

The cloning of chromosomal translocation breakpoints in sarcomas has begun to provide insights into their pathogenesis and is opening new avenues for molecular diagnosis. The sarcoma translocations cloned so far appear to involve transcription factor genes (Delattre et al., 1992; Zucman et al., 1993; Sorensen et al., 1994; Galili et al., 1993 and Shapiro et al., 1993). The oncogenicity of chimeric transcription factors resulting from tumor-specific translocations is a common theme in hematologic neoplasms (Cleary, 1991). The promiscuous pairing of the EWS gene with other genes may thus determine the phenotype of several primitive sarcomas. The situation appears analogous to the pairing of the MLL/HRX gene with various partners in different types of acute leukemia (Forster et al., 1993 and Hunger et al., 1993). The further elucidation of the pathogenesis of DSCRT, a tumor type characterized by divergent, multilineage differentiation should be particularly interesting.

EXAMPLE 2

Isolation and characterization of a EWS-WT1 genomic DNA junction fragment from DSRCT. Further to experiments in EXAMPLE 1 wherein nongermline DNA fragments were identified in multiple restriction enzyme digests of genomic DNA from DSRCT that hybridize with both EWS-WT1 and WT1-specific probes. DNA from one such tumor (DSRCT case 3) was used to produce a genomic library, size-selected for a rearranged BamHI fragment. This fragment was chosen for cloning due to its relatively large size and clear separation from germline EWS-containing BamHI fragments (FIG. 5A). A EWS cDNA probe was used for library screening and identified a clone containing the expected size DNA fragment. The insert fragment hybridized to both EWS and WT1 specific probes and comparison of restriction map data indicated a fusion of the two genes with expected breakpoints within the intron between exons 7 and 8 of EWS and the intron between exons 7 and 8 of WT1 (FIG. 5B). Sequencing using the cloned fragment as template and primers directed to EWS exon 8 (primers EWS 8.1 and EWS 8.2, Table 2) and WT1 exon 7 (primers WT1 7.1 and WT1 7.2, Table 2) showed that both exons were intact without mutation of the coding sequences. This DSRCT-specific rearranged DNA fragment therefore represented fusion of the 5' end of the WT1 gene on chromosome 11 to the 3' end of EWS on chromosome 22. Although cytogenetic analysis was not performed in the tumor from which this DNA was isolated, this junction fragment is expected to correspond to the derivative chromosome 11 of the DSRCT-associated t(11;22) because of the centromere 5'-3' telomere orientation of both EWS and WT1. Detailed restriction mapping and sequencing indicate that the breakpoints are approximately 3.5 kb from the 3' end of WT1 exon 7 and less than 1 kb from the 5'end of EWS exon 8. The EWS breakpoint site identified in this DSRCT junction fragment is located within a region commonly involved by other EWS-related tumor specific chromosomal translocations (Zucman et al., 1993). Consistent translocations involving the WT1 gene have not been described.

Analysis of chimeric transcripts in DSRCT. Primers designed to amplify cDNA spanning the junction region of potential transcripts from this EWS-WT1 gene fusion were used to analyze RNA from six DSRCT by reverse transcriptase-PCR (RT-PCR). Primers corresponding to the 5' portion of EWS (EWS 22.3, Table 2) and 3' portion of WT1 (WT1 10.1, Table 2) resulted in amplification of a 268 bp product in four out of six DSRCT (FIG. 6, results for five cases shown, cases 3,4 and 5 are positive. RT-PCR did detect a chimeric transcript in RNA from case 6, but insufficient RNA was isolated for complete analysis). The size of the RT-PCR product is consistent with fusion of EWS exon 7 to WT1 exon 8 as expected from the location of the breakpoint sites identified in the cloned junction fragment. Indeed, sequencing of PCR products from all four positive tumors revealed identical in frame fusions of EWS exon 7 to WT1 exon 8 (FIG. 7B, SEQUENCE ID NO. 19). No mutations of the junctional exon sequences were identified. The potential reciprocal translocation RNA transcript corresponding to the derivative chromosome 22 and consisting of 5' WT1 and 3' EWS exons was not detected by RT-PCR (primers WT1-EWS 1.0 and WT1-EWS 2.0, Table 2, 209 bp expected product) in any DSRCT (FIG. 6). These data suggest that DSRCTs typically have genetic alterations resulting in fusion of EWS to WT1 and the breakpoints consistently involve the same introns as those identified in the cloned junction fragment. A likely reason for the lack of detection of chimeric transcripts in some examples of DSRCT is sampling error due to the very low quantity and focal distribution of neoplastic cells present in some samples from these fibroblast rich tumors, however the possibility that breakpoint sites are different or absent requires further study. The predicted chimeric product is therefore composed of the first seven exons of EWS, encoding the potential transcription modulating domain, and exons 8, 9, and 10 of WT1, encoding the last three zinc-fingers of the DNA-binding domain (FIG. 7A). Chimeric transcripts were not detected in RNA isolated from normal tissue or other tumor types including a Wilms' tumor that expresses high levels of WT1 and a Ewing's sarcoma that demonstrates EWS-FLI1 chimeric transcripts (FIG. 6).

Appropriate combinations of the same primers were used to identify the wild type transcripts from WT1 (primers WT1 10.1 and WT1-EWS 2.0, Table 2, expected product 315 bp) and EWS (primers EWS 22.3 and WT1-EWS 1.0, Table 2, expected product 162 bp). FIG. 6 shows that the wild type WT1 transcript is present in the five DSRCTs evaluated, including one case that produces amplification products at similar levels to the control Wilms' tumor. Since low levels of WT1 are produced by some mature non-neoplastic tissues, the proportion of these transcripts produced by neoplastic cells versus what represents expression from contaminating non-neoplastic cells is not known (FIG. 6; Haber et al., 1991; Tadokoro et al., 1992; Plougastel et al., 1993; Pritchard-Jones eta., 1990; and Pritchard-Jones et al., 1991). The wild type EWS product was present in all tumors and tissues analyzed as might be expected for this ubiquitously expressed gene.

WT1 alternative splice sites are used by the chimeric transcript. The WT1 gene encodes four alternatively spliced RNA transcripts that produce functionally different products (Haber et al., 1991). One alternative splice site is located at the 3' end of exon 9 and leads to products that differ by three amino acids placed between the third and fourth zinc fingers of the DNA binding domain (plus [ID SEQUENCE NO. 20] or minus [ID SEQUENCE NO. 21] lysine, threonine and serine[+or−KTS]) (FIG. 7A). These two forms of WT1 have been shown to have different sequence specific binding properties (Rauscher et al., 1990; Madden et al., 1991; and Bickmore et al., 1992). Because the DSRCT specific chimeric transcripts include this region of WT1, the presence of alternatively spliced chimeric RNA was examined. Primers specific for each alternatively spliced transcript were used in RT-PCR assays (primers EWS 22.3, SEQUENCE ID NO. 1; and either WT1+KTS SEQUENCE ID NO. 10, or WT1−KTS SEQUENCE ID NO. 11, Table 2, expected products 254 and 245 bp respectively). Both potential transcripts were detected in the cases of DSRCT that had been shown to produce chimeric transcripts and confirmed by sequence analysis of the PCR products (FIG. 6). This result is in keeping with previous studies showing that +and −KTS transcripts are present in all normal and tumor tissues expressing the WT1 gene (Haber et al., 1991; and Brenner et al., 1992). The presence of both splice variants implies that the genetic fusion of EWS to WT1 has not altered the integrity of the +and −KTS alternative splice sites and both chimeric proteins are potentially expressed in DSRCT.

These studies document the functional fusion of the EWS and WT1 genes in DSRCT. EWS is known to participate in several tumor-related chromosomal translocations, but this is the first instance in which a specific tumor type has been consistently associated with translocation of WT1. This unique rearrangement generates a hybrid molecule that closely resembles the products of other EWS-related tumor specific gene fusions. The EWS gene was identified as the site disrupted by the chromosomal translocation t11;22) (q24;q12) found in Ewing's sarcoma and primitive neuroectodermal tumor (Zucman et al., 1992). It encodes a widely expressed 656-amino-acid protein composed of an amino terminal domain homologous to eukaryotic RNA polymerase II and a carboxy terminal region with homology to RNA-binding domains. The translocation partners of EWS are postulated to function as transcription factors (Delattre et al., 1992; Zucman et al., 1993; and Sorensen et al., 1994). In each case it appears that translocation results in chimeric products containing the amino-terminal domain of EWS fused to the nucleic acid binding domain of the translocation partner. EWS-FLI1 fusion products have been shown to be potent transcriptional activators and efficiently transform NIH 3T3 cells (May et al., 1993; May et al., 1993; and Ohno et al., 1994). The amino terminal domain of EWS is required for both these activities and from breakpoint mapping studies, this domain is preserved in all EWS-related translocation fusions including DSRCT. The previously described translocation partners of EWS contribute either the ETS-related DNA binding domain of FLI1 or ERG in the Ewing's sarcoma/primitive neuroectodermal family of tumors, or the bZIP protein dimerization and DNA-binding domain of ATF-1 in clear cell sarcoma of soft tissue (Delattre et al., 1992; Zucman et al., 1993 and Sorensen et al., 1994). In the case of DSRCT the EWS-WT1 hybrid products are expected to include the last three zinc-fingers of the DNA-binding domain of WT1. The WT1 zinc finger region is highly homologous to that of the early growth response (EGR) family of proteins and one alternatively spliced form of WT1 binds to consensus DNA binding sites for these proteins (Haber and Buckler, 1992 and Haber and Housman, 1992). The specific function and targets of WT1 are not known but WT1 represses transcription from several genes with EGR 1-like promoter regions (PDGF A-chain, IGF-2 and EGR-1), and mutations affecting the zinc finger regions abolish this function (Rauscher et al., 1990; Madden et al., 1991; Bickmore et al., 1992; Gashler et al., 1992; and Drummond et al., 1992). However, the DNA-binding domain of WT1 is different in two respects: 1) it contains one additional zinc finger domain that is, interestingly, not included in the DSRCT chimeric product and 2) the presence of an alternative splice site at the 3' end of exon 9 (zinc-finger 3), that introduces three amino acids into a strongly conserved spacing between zinc fingers and alters the sequence specific DNA binding properties of the protein (Bickmore et al., 1992; and Drummond et al., 1992). The +KTS form is the most abundant form in tissues and tumors expressing WT1, and binds DNA sequences different from the consensus EGR target. Both alternative splice variants were detected in DSRCT implying that the chimeric product is capable of interacting with a full spectrum of WT1-specific DNA target sequences.

In light of the proposed transcriptional activation function of the amino-terminal domain of EWS, that certain naturally occurring tumor-associated alterations of WT1 function convert it to a transcriptional activator. Two mutations affecting the amino terminal portion of WT1 have been shown to encode transcriptional activators and one of these mutations was identified in a mesothelioma, a tumor type that like DSRCT involves serosal surfaces (Park et al., 1993; and Park et al., 1993). In addition, tumor specific aberrant splicing of WT1 resulting in deletion of exon 2 has recently been identified in many Wilms' tumors but not normal tissues. The altered protein product, in contrast to wild-type WT1, has transcriptional activation function and fails to suppress growth of tumor cells (Haber et al., 1993). This may represent a distinct and apparently common mechanism of WT1 functional alteration in Wilms' tumors. The WT1 gene product has also been shown to interact with p53, a tumor suppressor gene that is frequently deleted and mutated in a variety of tumors (Maheswaran et al., 1993). This interaction modulates the function of both proteins such that in the presence of wild-type p53, WT1 acts as a transcriptional repressor while in the absence of wild-type p53, WT1 is a potent transcriptional activator. These lines of evidence suggest that transcriptional activation of WT1 target genes can contribute to the malignant phenotype and this may be the oncogenic mechanism for the EWS-WT1 chimera in DSRCT.

The involvement of this particular combination of genes has many implications for the histo- and pathogenesis of DSRCT. The age of presentation and primitive appearance of the neoplastic cells in DSRCT is reminiscent of Ewing's sarcoma but the location, pattern of spread and immunohistochemical profile are unique. The normal function of the EWS gene is unknown, but it may be that in tumors associated with translocation of EWS the timing of tumor development is dependent on the regulatory and functional elements of the EWS gene and the cellular phenotype is more dependent on the target sites of the translocation partner. WT1 is expressed in structures derived from the intermediate mesoderm, primarily in tissues undergoing transition from mesenchyme to epithelium such as metanephric mesenchyme to nephron, mesenchyme lining the coelem to mesothelium and mesenchyme of the primitive gonad to sex cord elements (Pritchard-Jones et al., 1990; Pritchard-Jones and Fleming, 1991; Sharma et al., 1992; and Park et al., 1993). It is postulated that WT1 is expressed in a specific period of development as a signal for precursor cells to cease dividing and differentiate. It is likely to be related to a process whose key event is a change in phenotype of the mesenchymal cells to become epithelial in response to induction. The WT1 gene, therefore, is likely to encode a transcription factor intimately associated with a particular period in normal development of specific tissues, whose alteration may contribute to tumor formation in the primitive cells expressing this gene. This proposed oncogenic function fits well with the speculated histogenesis of DSRCT and would suggest that this tumor and its variants arise in the primitive mesenchyme of the coelomic cavities or gonad.

The identification of the EWS-WT1 fusion in DSRCT lends further support to the oncogenic role of transcription modulating chimeric products in many hematopoietic and solid tumor types. The elucidation of specific pathogenetic contributions of each fusion gene will give insight into the development and maintenance of the malignant phenotype. The availability of specific molecular genetic markers of individual tumors also provides auxiliary methods for primary diagnosis and monitoring of patients, and identify potential targets of novel antineoplastic therapeutic strategies. Further characterization of the structural and functional attributes of the EWS-WT1 gene fusion will begin to provide an understanding of its role in tumor development.

EXAMPLE 3

The EWS-WT1 chimeric transcript was detected in 11 out of 12 DSRCT by RT-PCR using primers for EWS exon 7 and WT1 exon 10. Ten of the 11 positive cases showed amplification of the expected 268 and 259 bp products corresponding to the two described splice variants of this portion of the WT1 gene (FIG. 8). Cloning and sequencing of PCR products in these cases showed in-frame fusions of EWS exon 7 to WT1 exon 8 (FIG. 9). Both splice variants (plus or minus 9 bp encoding lysine, threonine, serine [+KTS and −KTS]) were identified after sequencing multiple individual clones of the amplified chimeric transcript fusion fragments. No mutations in the segments close to the junction were seen. The full length chimeric product in these cases included the first 7 exons of EWS, an effector domain with strong transactivating properties in vitro, and exons 8 to 10 of WT1, that encode the last three zinc fingers of the DNA binding domain of WT1 (FIG. 9).

In a single case of DSRCT, RT-PCR for EWS-WT1 carried out using primers for EWS exon 7 and WT1 exon 10, yielded 442 bp (−KTS) and 451 bp (+KTS) DNA fragments (FIG. 8). Cloning and sequencing of these fragments confirmed a different chimeric transcript junction. Alignment of the sequence with wild type EWS and WT1 showed fusion of EWS exon 8 to WT1 exon 8. Therefore the chimeric transcript in this variant case differed from the typical chimeric product by including EWS exon 8. In addition, a 4 bp deletion at the 5' end of WT1 exon 8 and a 6 bp insertion in the junction between EWS and WT1 were present, resulting in an in-frame fusion of the two genes (FIG. 9). RT-PCR using primers complementary to EWS exon 8 and WT1 exon 9 detected chimeric transcripts only in this case, and not in any other DSRCT.

EWS-WT1 chimeric transcripts were not detected in any of the Ewing's sarcomas/PNET, Wilms' tumors, and rhabdomyosarcomas (FIG. 8). Results are summarized in Table 4.

RNA from seven of 13 alveolar rhabdomyosarcomas directed amplification of a 436 bp fragment by RT-PCR using primers for PAX3 and FKHR (Table 3). In addition 2 other alveolar rhabdomyosarcomas showed amplification of a 695 bp fragment with primers for PAX7-FKHR. These are the expected sizes of PCR products from the PAX3-FKHR and PAX7-FKHR chimeric transcripts (Galili et al., 1993 and Davis et al., 1994). All nine cases had been classified histologically as of alveolar type. Cloning and sequencing of these PCR products confirmed the PAX3-FKHR or PAX7-FKHR gene fusions. None of the nine rhabdomyosarcomas classified as the embryonal type showed amplification of the PAX3-FKHR or PAX7-FKHR products. RNA from DSRCT, Ewing's sarcomas, Wilms' tumors, and PNET did not yield PAX3-FKHR or PAX7-FKHR RT-PCR products.

All 8 Ewing's sarcomas and the two PNET demonstrated the presence of the EWS-FLI-1 chimeric transcript by RT-PCR (FIG. 8). All other tumors, including DSRCT, were negative for EWS-WT1FL I-1 chimeric transcript.

This demonstrates that RT-PCR detection of EWS-WT1 chimeric transcripts represents a very sensitive and specific molecular marker for DSRCT, being that these transcripts were not present in any of 49 other tumors considered in its differential diagnosis. The detection of chimeric transcripts has been shown to be very useful in the diagnosis of Ewing's sarcoma/PNET (Downing et al., 1993), and alveolar rhabdomyosarcoma (Tsokos, 1994). This example, using a panel of primers for individual chimeric RNA transcripts, delineated sharply each tumor type associated with that transcript.

The specificity of RT-PCR in the molecular diagnosis of DSRCT relies on the structure of the chimeric transcript which is composed of the first seven exons of EWS joined to the last three exons of WT1. The primers used direct amplification of a short segment close to the EWS-WT1 junction in this transcript, and correspond to the product of the derivative chromosome 22. In this example the fusion occurred between exon 7 of EWS, and exon 8 of WT1 in all cases except one. Molecular characterization of the latter tumor indicates that the chromosomal breakpoint is likely located in, or is distal to, the intron between exons 8 and 9 of EWS, and that the resulting chimeric transcript includes EWS exon 8. This tumor had a histologic appearance and immunophenotype typical of DSRCT, and indistinguishable from the others. Different breakpoint locations within EWS have been reported in Ewing's sarcoma/PNET, resulting in different types of chimeric transcripts (Downing et al., 1993 and Dockhorn-Dworniczak et al., 1994). However, this is the only known example of DSRCT with a chimeric transcript that includes EWS exon 8. Fusion of exon 8 of EWS to any exon of FLI-1 is out of frame, and extremely infrequent in Ewing's sarcoma/PNET (Zucman et al., 1993). Likewise, fusion of EWS exon 8 to WT1 exon 8 would result in an out of frame product. However, in the example described here,

TABLE 4

| Detection of chimeric transcripts in small round cell tumors. | | | | | | |
|---|---|---|---|---|---|---|
| Diagnosis | EWS-WT1 | EWS-FLI-1 | PAX3-FKHR | PAX7-FKHR | Negative | Total |
| DSRCT | 11 | 0 | 0 | 0 | 1 | 12 |
| Ewing's sarcoma | 0 | 8 | 0 | 0 | 0 | 8 |
| PNET | 0 | 2 | 0 | 0 | 0 | 2 |
| Wilm's tumor | 0 | 0 | 0 | 0 | 17 | 17 |
| Alveolar rhabdomyosarcoma | 0 | 0 | 7 | 2 | 4 | 13 |
| Non-alveolar rhabdomyosarcoma | 0 | 0 | 0 | 0 | 9 | 9 |
| Total | 11 | 10 | 7 | 2 | 31 | 61 | there is a small deletion of WT1 and insertion of 6 nucleotides at the junction of the chimeric transcript resulting in an in-frame product. The genomic breakpoint region from this case is currently being cloned and sequenced to further define this variant gene fusion. The prognostic and biological significance of this variant translocation in DSRCT, if any, remains unknown.

DSRCT is a tumor with unique clinical, morphological and immunohistochemical features (Gerald et al., 1991; and Gerald and Rosai, 1993). The clinicopathological spectrum of this tumor is, however, wider than initially reported (Gerald and Rosai, 1993 and Ordonez et al., 1993). There are 3 reported cases of DSRCT in a pleural location (Bian et al., 1993 and Parkash et al., 1995), and one in the posterior cranial fossa (Tison et al., in press). Some cases of DSRCT express MIC-2, a marker detected in most Ewing's sarcomas, although there are some differences in the subcellular distribution of this antigen between the two tumor types. Some cases of DSRCT have unusual histologic features such as little desmoplasia (Swanson et al., 1994), prominent tubular or gland-like formation (Gerald and Rosai, 1993), spindle cells areas, pseudorosette formation or foci of larger anaplastic cells (Gerald et al., 1991). For this reason a specific assay, like the detection of the EWS-WT1 chimeric transcript by RT-PCR, may prove to be useful for accurate classification and diagnosis of this member of the small round cell tumor family.

The EWS-WT1 chimeric transcript was not detected in one case. This may be due to sampling error, since the tumor contained rare foci of tumor cell nests; however the possibility of variant translocations or lack of EWS-WT1 fusion in this case should also be considered. Studies to assess the sensitivity of the test are in progress, although it is expected to be similar to that of RT-PCR for EWS-FLI-1, which is about one tumor cell in $10^4$–$10^5$ (Downing et al., 1993). Because of its high sensitivity, one of the potential utilities of RT-PCR to EWS-WT1 is to detect the presence of tumor cells in peripheral blood or ascitic fluid, thus allowing a more accurate staging, and more sensitive monitoring for residual or recurrent disease in patient follow up.

DSRCT is the third tumor type associated with translocation of the EWS gene. The others are Ewing's sarcoma/ PNET (Downing et al., 1993), and clear cell sarcoma of soft parts (Zucman et al., 1993), but only DSRCT is associated with a consistent translocation of WT1. All chimeric proteins encoded by gene fusions with EWS have a similar structure, with a transactivator domain in the amino-terminal region, and a DNA binding domain in the carboxy-terminal region. In each case the histologic tumor classification correlates with a different translocation partner of EWS. In DSRCT its chimeric protein is predicted to modulate transactivation at WT1 responsive genes. Interestingly the locations reported so far for DSRCT are related to the serosal lining of body cavities, a structure that, like the urogenital system, has a high transient fetal expression of the WT1 gene (Pritchard-Jones et al., 1990).

The specificity of molecular assays may be helpful in the differential diagnosis of small round cell tumors. An experiment supporting the utility of RT-PCR for the diagnosis of pediatric small round cell tumors was undertaken (Barr et al., 1995). One important potential use is in the differential diagnosis between DSRCT and Ewing's sarcoma-PNET since the latter are positive for EWS-FLI-1 or EWS-WT1ERG and consistently negative for EWS-WT1. The detection of the t(2;13) translocation (PAX3-FKHR transcript), and t(1;13) (PAX7-FKHR transcript) were very specific for alveolar rhabdomyosarcoma in our series. The sensitivity of this test was high, although 4/13 alveolar rhabdomyosarcomas were negative. Because certain gene rearrangements have proven to be very specific, it will be interesting to apply these analyses to some other subsets of developmental tumors like extraosseous Ewing's sarcomas (Navarro et al., 1994), extrarenal rhabdoid tumors (Kodet et al., 1991), polyphenotypic non-desmoplastic small cell tumors (Parkash et al., 1995), mesenchymal chondrosarcomas, and small cell osteosarcomas.

Molecular analysis of small round cell tumors of childhood has been very informative concerning tumor classification. Tumors formerly viewed as distinct entities such as PNET and Ewing's sarcoma have been shown to have similar genetic alterations, and probably belong to the same family (Barr et al., 1995; Dehner, 1994; Dehner, 1993; and Delattre et al., 1994). Alveolar and embryonal rhabdomyosarcomas are two different clinico-pathological entities associated with different genetic changes, and only share skeletal muscle differentiation (Tsokos, 1994). Molecular analysis, in conjunction with morphology and immunohistochemical data, will help to better define biologically homogeneous clinico-pathological entities, and provide a useful diagnostic tool for these aggressive developmental tumors.

References

1. Aurias, A., Rimbaut, C., Buffe, C., Dubousset, J. & Mazabraud, A. (1983) N. Engl. J. Med., 309:496–497.
2. Barr, F. G., Chatten, J., D'Cruz, C. M., Wilson, A. E., Nauta, L. E., Nycum, L. M., Biegel, J. A., Womer, R. B. (1995) JAMA, 273:553–557.
3. Barr, F. G., Galili, N., Holick, Biegel, J. A., Rovera, G., Emanuel, B. S. (1993) Nature Genetics, 3:113–117.
4. Bian, Y., Jordan, A. G., Rupp, M., Cohn, H., McLlaughlin, C. J., Miettinen, M. (1993) Acta Cytol, 37:77–82.
5. Bickmore, W. A., Oghene, K., Little, M., Seawright, A., van Heyningen, V. and Hastie, N. (1992) Science, 257:235–237.
6. Biegel, J. A., Conard, K., Brooks, J. J. (1993) Genes Chromosom. Cancer, 7:119–121.
7. Boehm, T., Foroni, L., Kaneko, Y., Perutz, M. F., Rabbitts, T. H. (1991) Proc. Natl. Acad. Sci. U.S.A., 88:4367–4371.
8. Bonetta, L., Kuehn, S. E., Huang, A., Law, D. J., Kalikin, L. M., Koi, M., Reeve, A. E., Brownstein, B. H., Yeger, H., Williams, B. R. & Feinberg, A. (1990) Science, 250:994–997.
9. Bonin, G., Scamps, C., Turc-Carel, C. & Lipinski M. (1993) Cancer Res., 53:3655–3657.
10. Brenner, B., Wildhardt, G., Schneider, S. and Royer-Pokora, B. (1992) Oncogene, 7:1431–1433.
11. Call, K. M., Glaser, T., Ito, C. Y., Buckler, A. J., Pelletier, J., Haber, D. A., Rose, E. A., Kral, A., Yeger, H., Lewis, W. H., Jones, C. (1990) Cell, 60:509–520.
12. Chomczynski, P. and Sacchi, N. (1987) Anal. Biochem., 162:156–159.
13. Cleary, M. L. (1991) Cell, 66:619–622.
14. Cohen J. S. (1989) Trends in Pharm. Sci., 10:435.
15. Crozat, A., Aman, P., Mandahl, N. and Ron, D. (1993) Nature, 363:640–644.
16. Davis, R. J., D'Cruz, C. M., Lovell, M. A., Biegel, J. A., Barr, F. G. (1994) Cancer Research, 54:2869–2872.
17. Dehner, L. P., (1994) Arch. Pathol. Lab. Med. (Editorial), 118:606–607.
18. Dehner, L. P., (1993) Am. J. Surg. Pathol., 17:1–13.
19. Delattre, O., Zucman, J., Melot, T., Sastre, X., Zucker, J. M., Lenoir, G. M., Ambros, P. F., Sheer, D., Turc-Carel, C., Triche, T., Aurias, A., Thomas, G. (1994) Engl. J. Med., 331:294–299.

20. Delattre, O., Zucman, J., Plougastel, B., Desmaze, C., Melot, T., Peter, M., Kovar, H., Joubert, I., de Jong, P., Rouleau, G., Aurias, A., Thomas, G. (1992) *Nature*, 359:162–165.

21. Dockhorn-Dworniczak, B., Schäfer, K. L., Dantcheva, R., Blasius, S., Winkelmann, W., Strehl, S., Burdach, S., van Valen, F., Jergens, H., Böcker, W. (1994) *Virchows Archiv*, 425:107–112.

22. Douglass, E. C., Valentine, M., Etcubanas, E, Parham, D., Webber, B. L., Houghton, P. J., Houghton, J. A. and Green, A. A. (1987) *Cytogenet. Cell Genet.*, 45:148–155.

23. Downing, J. R., Head, D. H., Parham, D. M., Douglass, E. C., Hulshof, M. G., Link, M. P., Motroni, T. A., Grier, H. E., Curcio-Brint, A. M., Shapiro, D. N. (1993) *Am. J. Pathol.*, 143:1294–1300.

24. Drummond, I. A., Madden, S. L., Rohwer-Nutter, P., Bell, G. I., Sukhatme, V. P. and Rauscher, F. J. III. (1992) *Science*, 257: 674–678.

25. Drummond, I. A., Rupprecht, H. D., Rohwer-Nutter, P., Lopez-Guisa, J. M., Madden, S. L., Rauscher, F. J. III, Sukhatme, V. P. (1994) *Molec. & Cellul. Biol.*, 14: 3800–3809.

26. Forster, A., Thompson, S., Lampert, F., Kaneko, Y., Slater, R., Kroes, W. G., vander Schoot, C. E., Ludwig, W. D., Karpas, A., Pocock, C., Cotter, F., Rabbitts, T. H. (1993) *Proc. Natl. Acad. Sci. U.S.A.*, 90:8538–854.

27. Galili, N., Davis, R. J., Fredericks, W. J., Mukhopadyay, S., Rauscher, F. J. III., Emanuel, B. S., Rovera, G. and Barr, F. G. (1993) *Nature Genet.*, 5:230–235.

28. Gashler, A. L., Bonthron, D. T., Madden, S. L., Rauscher, F. J. 3d., Collins, T. & Sukhatme, V. P. (1992) *Proc. Natl. Acad. Sci. U.S.A.*, 89:6010–6014.

29. Gerald, W. L., Chao, J., and Chao, L. (1986) *Biochim. and Biophys., Acta*, 866:1–14.

30. Gerald, W. L., Gramling, T. S., Sens, D. A., Garvin, A. J. (1992) *Am. J. Pathol.*, 140:1031–1037.

31. Gerald, W. L., Miller, H. K., Battifora, H., Miettinen, M., Silva, E. G., Rosai, J. (1991) *Am. J. Sur. Pathol.*, 15:499–513.

32. Gerald, W. L. and Rosai, J. (1993) *Zentralbl. Pathol.*, 139:141–151.

33. Gerald, W. L. and Rosai, J. (1993) *Zentrabl. Pathol.*, 139: 141–152.

34. Gerald, W. L., Rosai, J., Case 2. (1989) *Pediatr. Pathol.*, 9:177–183.

35. Gessler, M., Konig, A., Bruns, G. A. (1992) *Genomics*, 12:807–813.

36. Gessler, M., Pustka, A, Cavenee, W., Neve, R. L., Orkin, S. H. and Bruns, G. A. (1990) *Nature*, 343:774–778.

37. Haber, D. A. and Buckler, A. J. (1992) *The New Biol.*, 4: 97–106.

38. Haber, D. A. and Housman, D. E. (1992) *Cancer Survey*, 12: 105–117.

39. Haber, D. A., Park, S., Maheswaran, S., Englert, C., Re, G. G., Hazen-Martin, D. J., Sens, D. A. and Garvin, A. J. (1993) *Science*, 262:2057–2059.

40. Haber, D. A., Sohn, R. L., Buckler, A. J., Pelletier, J., Call, K. M., Housman, D. E. (1991) *Proc. Natl. Acad. Sci. U.S.A.*, 88:9618–9622.

41. Hunger, S. P., Tkachuk, D. C., Amylon, M. D., Link, M. P., Carroll, A. J., Welborn, J. L., Willman, C. L., Cleary, M. L. (1993) *Blood*, 81:3197–3203.

42. Kodet, R., Newton, W. A., Sachs, N., Hamoudi, A. B., Raney, R. B., Asmar, L., Gehan, E. (1991) *Hum. Pathol.*, 22:674–684.

43. Ladanyi, M., Lewis, R., Garin-Chesa, P., Rettig, W. J., Huvos, A. G., Healey, J. H., Jhanwar, S. C. (1993) *Diag. Mol. Pathol.*, 2:141–146.

44. lange W., Daskalakis, M., Finke J., and Dolken G. (1994) *FEBS Lett.* 338:175–188.

45. Madden, S. C., Cook, D. M., Morris, J. F., Gashler, A., Sukhatme, V. P. and Rauscher, F. J. III. (1991) *Science*, 253:1550–1553.

46. Maheswaran, S., Park, S., Bernard, A., Morris, J. F., Rauscher, F. J. III, Hill, D. E. and Haber, D. A. (1993) *Proc. Natl. Acad. Sci. U.S.A*, 90:5100–5104.

47. Maniatis, T., Fritsch, E. F., and Sambrook, J. (1982). Molecular Cloning: A Laboratory Manual, Cold Spring Harbor Laboratory, Cold Spring Harbor, N.Y.

48. May, W. A., Gishizky, M. L., Lessnick, S. L., Lunsford, L. B., Lewis, B.C., Delattre, O., Zucman, J., Thomas, G. and Denny, C. T. (1993) *Proc. Natl. Acad. Sci. U.S.A.*, 90:5752–5756.

49. May, W. A., Lessnick, S. L., Braun, B. S., Klemsz, M., Lewis, B. C., Lunsford, L. B., Hromas, R. and Denny, C. T. (1993) *Molec. & Cellul. Biol.*, 13:7393–7398.

50. Navarro, S., Cavazzana, A. O., Llombart-Bosch, A., Triche, T. J. (1994) *Arch. Pathol. Lab. Mede*, 118:608–615.

51. Ohno, T., Rao, V. N. and Reddy, E. S. P. (1994) *Cancer Res.*, 53:5859–5863.

52. Ordoñez, N. G., El-Naggar, A. K., Ro, J. Y., Silva, E. G., MacKay, B. (1993) *Hum. Pathol.*, 24:850–865.

53. Ordoñez, N.G., Zirkin, R., Bloom, R. E. (1989) *Am. J. Surg. Pathol.*, 13:413–421.

54. Park, S., Schalling, M., Bernard, A., Maheswaran, S., Shipley, G. C., Roberts, D., Fletcher, J., Shipman, R., Rheinwald, J., Demetri, G., Griffin, J., Minden, M., Housman, D. and Haber, D. (1993) *Nature Genet.*, 4:415–420.

55. Park, S., Tomlinson, G., Nisen, P. and Haber, D. A. (1993) *Cancer Res.*, 53:4757–4760.

56. Parkash, V., Gerald, W. L., Parma, A., Miettinen, M., Rosai, J. (1995) *Am. J. Surg. Pathol.*, (in press).

57. Plougastel, B., Zucman, J., Peter, M., Thomas, G., Delattre, O. (1993) *Genomics*, 18:609–615.

58. Pritchard-Jones, K. and Fleming, S. (1991) *Oncogene*, 6: 2211–2220.

59. Pritchard-Jones, K., Fleming, S., Davidson, D., Bickmore, W., Porteus, D., Gosden, C., Bard, J., Buckler, A., Pelletier, J., Housman, D., van Heyningen, V., Hastie, N. (1990) *Nature*, 346:194–197.

60. Rauscher, F. J. III, Morris, J. F., Tournay, O. E., Cook, D. M. and Curran, T. (1990) *Science*, 250:1259–1262.

61. Rodríguez, E., Sreekantaiah, C., Gerald, W., Reuter, V. E., Motzer, R. J., Chaganti, R. S. K. (1993) *Cancer Genet. Cytogenet.*, 69:17–21.

62. Royer-Pokora, B., Loos, U., Ludwig, W. D. (1991) *Oncogene.*, 6:1887–1893.

63. Sambrook, J., Fritsch, E. F., Maniatis, T. (1989) A laboratory Manual, Second Edition (Cold Spring Harbor: CSH Laboratory Press).

64. Sanger, F., Nicklen, S., Coulson, A. R. (1977) *Proc. Natl. Acad. Sci. U.S.A.*, 74:5463–5467.

65. Sawyer, J. R., Tryka, A. F., Lewis, J. M. (1992) *Am. J. Surg. Pathol.*, 16:411–416.

66. Shapiro, D., Sublett, J. E., Li, B., Downing, J. R., Naeve, C. W. (1993) *Cancer Res.*, 53:5108–5112.

67. Sharma, M., Yang, X., Bowman, M., Roberts, V. and Sukumar, S. (1992) *Cancer Res.*, 52:6407–6412.

68. Shen, W. P., Towne, B., Zadeh, T. M. (1992) *Cancer Genet. Cytogenet.*, 64:189–191.

69. Sorensen, P. H. B., Lessnick, S. L., Lopez-Terrada, D., Liu, X. F., Triche, T. J., Denny, C. T. (1994) *Nature Genet.*, 6:146–151.

70. Swanson, P. .E., Wick, M. R., Garíin-Chesa, P., Dehner, L. P. (1994) *Lab. Invest.*, 70:11A (abstract).
71. Tadokoro, K., Oki, N., Fujii, H., Ohshima, H., Inove, T. and Yamada, M. (1992) Jpn. J. *Cancer Res.*, 83: 1198–1203.
72. Tison, V., Cerasoli, S., Cenacchi, G., Morigi, F., Ladanyi, M., Gerald, W. L., Rosai, J. *Am. J. Surg. Pathol.*, (in press).
73. Ton, C. C., Hirvonen, H., Miwa, H., Weil, M. M., Monaghan, P., Jordan, T., van, H., V, Hastie, N. D., Meijers-Heijboer, H., Drechsler, M., Royer-Pokora, B., Collins, F., Swaroop, A., Strong, L. C., Saunders, G. F. (1991) *Cell*, 67:1059–1074.
74. Tsokos, M. (1994) *Sem. Diagn. Pathol.*, 11:26–38.
75. Turc-Carel, C., Aurias, A., Mugneret, F., Lizard, S., Sidaner, I., Volk, C., Thiery, J. P., Olschwang, S., Philip, I., Berger, M. P., Phillip, T., Lenoir, G. and Mazabraud, A. (1988) *Cancer Genet. Cytogenet.*, 32: 229–238.
76. Turc-Carel, C., Lizard-Nacol, S., Justrabo, E., Favrot, M., Philip, T. and Tabone, E. (1986) *Cancer Genet. Cytogenet.*, 19:361–362.
77. Turc-Carel, C., Philip, I., Berger, M. P., Philip, T. and Lenoir, G. M. (1983) *N. Engl. J. Med.*, 309:497–498.
78. Wang-Wu, S., Soukup, S., Ballard, E., Gotwals, B. and Lampkin, B. (1988) *Cancer Res.*, 48:983–987.
79. Weintraub, H. M. (1990) *Sci. Am., January p.* 40.
80. Whang-Peng, J., Triche, T. J., Knutsen T, Miser, J., Douglass, E. C. and Israel, M. A. (1984) *N. Engl. J. Med.*, 311:584–585.
81. Yeger, H., Cullinane, C., Flenniken, A., Chilton-MacNeil, S., Campbell, C., Huang, A., Bonetta, L., Coppes, M. J., Thorner, P., Williams, B. R. (1992) *Cell Growth Differ.*, 3:855–864.
82. Zucman, J., Delattre, O., Desmaze, C., Epstein, A., Stenman, G., Speleman, F., Fletchers, C. D. M., Aurias, A., Thomas, G. (1993) *Nature Genet.*, 4:341–345.
83. Zucman, J., Delattre, O., Desmaze, C., Plougastel, B., Joubert, I., Melot, T., Peter, M., De Jong, P., Rouleau, G., Aurias, A., Thomas, G. (1992) *Genes Chromos. Cancer*, 5:271–277.
84. Zucman, J., Melot, T., Desmaze, C., Ghysdael, J., Plougastel, B., Peter, M., Zucker, J. M., Triche, T. J., Sheer, D., Turc-Carel, C., Ambros, P., Combaret, V., Lenoir, G., Aurias, A., Thomas, G. & Delattre, O. (1993) *EMBO Journal*, 12:4481–4487.

---

What is claimed is:

1. A method of diagnosing a desmoplastic small round cell tumor in a subject which comprises detecting in a sample from the subject a nucleic acid molecule encoding a chimeric EWS-WT1 protein, positive detection indicating the presence of desmoplastic small round cell tumor.

2. The method of claim 1, wherein the nucleic acid molecule encoding the chimeric EWS-WT1 protein is detected by size fractionation.

3. The method of claim 2, wherein the size fractionation is effected by a polyacrylamide or an agarose gel.

4. The method of claim 1, wherein the detection of the nucleic acid molecule encoding the chimeric EWS-WT1 protein comprises contacting the nucleic acid molecule from the sample with an EWS, WT1 or a chimeric EWS-WT1 probe capable of hybridizing with the nucleic acid molecule encoding the chimeric EWS-WT1 protein, wherein the probe is labeled with a detectable marker under conditions permitting the EWS, WT1 or the chimeric EWS-WT1 probe to hybridize with the nucleic acid molecule encoding the chimeric EWS-WT1 protein, thereby detecting the nucleic acid molecule encoding the chimeric EWS-WT1 protein.

5. The method of claim 4, wherein the detectable marker is a radiolabeled molecule, a fluorescent molecule, an enzyme, or a ligand.

6. The method of claim 1, wherein the detection of the nucleic acid molecule encoding the chimeric EWS-WT1 protein comprises amplifying the nucleic acid molecule encoding the chimeric EWS-WT1 protein, thereby detecting the nucleic acid molecule encoding the chimeric EWS-WT1 protein.

7. The method of claim 6, wherein the amplification of the nucleic acid molecule encoding the chimeric EWS-WT1 protein comprises contacting the nucleic acid molecule from the sample with at least two primers bracketing a translocation breakpoint of a t(11;22) (p13;q12) translocation under conditions for polymerase chain reaction.

8. The method of claim 6, wherein the nucleic acid molecule encoding the chimeric EWS-WT1 protein is detected by size fractionation.

9. The method of claim 8, wherein the size fractionation is effected by a polyacrylamide or an agarose gel.

10. The method of claim 6, wherein the detection of the nucleic acid molecule encoding the chimeric EWS-WT1 protein comprises contacting the nucleic acid molecule encoding the chimeric EWS-WT1 protein with an EWS, WT1, or a chimeric EWS-WT1 probe capable of hybridizing with the nucleic acid molecule encoding the chimeric EWS-WT1 protein, wherein the probe is labeled with a detectable marker under conditions permitting the EWS, WT1, or the chimeric EWS-WT1 probe to hybridize with the nucleic acid molecule encoding the chimeric EWS-WT1 protein, detecting hybridization of the nucleic acid molecule encoding the chimeric EWS-WT1 protein with the probe, thereby detecting the nucleic acid molecule encoding the chimeric EWS-WT1 protein.

11. The method of claim 10, wherein the detectable marker is a radiolabeled molecule, a fluorescent molecule, an enzyme, or a ligand.

* * * * *

SEQUENCE LISTING ( 1 ) GENERAL INFORMATION:

( i i i ) NUMBER OF SEQUENCES: 21

( 2 ) INFORMATION FOR SEQ ID NO:1:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

TCCTACAGCC AAGCTCCAAG TC        22

( 2 ) INFORMATION FOR SEQ ID NO:2:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

GCATGAGTGG CCCTGATAAC        20

( 2 ) INFORMATION FOR SEQ ID NO:3:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

ATTCCACCGC GTCCTCCTCC 20

( 2 ) INFORMATION FOR SEQ ID NO:4:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

GCCACCGACA GCTGAAGGGC 20

( 2 ) INFORMATION FOR SEQ ID NO:5:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

GACACTGAAC GGTCCCCGA 19

( 2 ) INFORMATION FOR SEQ ID NO:6:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

CTTACCAGTG TGCTTCCTGC 20

( 2 ) INFORMATION FOR SEQ ID NO:7:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

CTTCCTCTTA CTCTCTGCCT GC 22

( 2 ) INFORMATION FOR SEQ ID NO:8:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

GTTATCAGGG CCACTCATGC 20

( 2 ) INFORMATION FOR SEQ ID NO:9:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:9:

CATCTGAGAC CAGTGAGAAA CG      22

( 2 ) INFORMATION FOR SEQ ID NO:10:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

AAGGGCTTTT CACTTGTTTT AC      22

( 2 ) INFORMATION FOR SEQ ID NO:11:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:11:

AAGGGCTTTT CACCTGTATG AG      22

( 2 ) INFORMATION FOR SEQ ID NO:12:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:12:

ACTCCCCGTT GGTCCCCTCC      20

( 2 ) INFORMATION FOR SEQ ID NO:13:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:13:

GCACTGTACA CCAAAGCACG      20

( 2 ) INFORMATION FOR SEQ ID NO:14:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:14:

TTTGAGAGGA CCCACTACCC                                                                      20

( 2 ) INFORMATION FOR SEQ ID NO:15:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:15:

AACTGTGATC CAGGGCTGTC                                                                      20

( 2 ) INFORMATION FOR SEQ ID NO:16:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:16:

ACCTTCGTTC ACAGTCCTTG                                                                      20

( 2 ) INFORMATION FOR SEQ ID NO:17:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:17:

GACCAGGAGA ACTTTCGCTG AC                                                                   22

( 2 ) INFORMATION FOR SEQ ID NO:18:

( i ) SEQUENCE CHARACTERISTICS:
        ( A ) LENGTH: 2412 base pairs
        ( B ) TYPE: nucleic acid
        ( C ) STRANDEDNESS: single
        ( D ) TOPOLOGY: linear ( i i ) MOLECULE TYPE: cDNA to mRNA ( x i ) SEQUENCE DESCRIPTION: SEQ ID NO:18:

GAGAACGAGG AGGAAGGAGA GAAAATGGCG TCCACGGATT ACAGTACCTA TAGCCAAGCT            60

GCAGCGCAGC AGGGCTACAG TGCTTACACC GCCCAGCCCA CTCAAGGATA TGCACAGACC          120

ACCCAGGCAT ATGGGCAACA AAGCTATGGA ACCTATGGAC AGCCCACTGA TGTCAGCTAT          180

ACCCAGGCTC AGACCACTGC AACCTATGGG CAGACCGCCT ATGCAACTTC TTATGGACAG          240

CCTCCCACTG GTTATACTAC TCCAACTGCC CCCCAGGCAT ACAGCCAGCC TGTCCAGGGG          300

TATGGCACTG GTGCTTATGA TACCACCACT GCTACAGTCA CCACCACCCA GGCCTCCTAT          360

GCAGCTCAGT CTGCATATGG CACTCAGCCT GCTTATCCAG CCTATGGGCA GCAGCCAGCA          420

GCCACTGCAC CTACAAGACC GCAGGATGGA AACAAGCCCA CTGAGACTAG TCAACCTCAA          480

```
TCTAGCACAG GGGGTTACAA CCAGCCCAGC CTAGGATATG GACAGAGTAA CTACAGTTAT       540
CCCCAGGTAC CTGGGAGCTA CCCCATGCAG CCAGTCACTG CACCTCCATC CTACCCTCCT       600
ACCAGCTATT CCTCTACACA GCCGACTAGT TATGATCAGA GCAGTTACTC TCAGCAGAAC       660
ACCTATGGGC AACCGAGCAG CTATGGACAG CAGAGTAGCT ATGGTCAACA AAGCAGCTAT       720
GGGCAGCAGC CTCCCACTAG TTACCCACCC CAAACTGGAT CCTACAGCCA AGCTCCAAGT       780
CAATATAGCC AACAGAGCAG CAGCTACGGG CAGCAGAGTG AGAAACCATA CCAGTGTGAC       840
TTCAAGGACT GTGAACGAAG GTTTTCTCGT TCAGACCAGC TCAAAAGACA CCAAAGGAGA       900
CATACAGGTG TGAAACCATT CCAGTGTAAA ACTTGTCAGC GAAAGTTCTC CCGGTCCGAC       960
CACCTGAAGA CCCACACCAG GACTCATACA GGTAAAACAA GTGAAAAGCC CTTCAGCTGT      1020
CGGTGGCCAA GTTGTCAGAA AAAGTTTGCC CGGTCAGATG AATTAGTCCG CCATCACAAC      1080
ATGCATCAGA GAAACATGAC CAAACTCCAG CTGGCGCTTT GAGGGGTCTC CCTCGGGGAC      1140
CGTTCAGTGT CCCAGGCAGC ACAGTGTGTG AACTGCTTTC AAGTCTGACT CTCCACTCCT      1200
CCTCACTAAA AAGGAAACTT CAGTTGATCT TCTTCATCCA ACTTCCAAGA CAAGATACCG      1260
GTGCTTCTGG AAACTACCAG GTGTGCCTGG AAGAGTTGGT CTCTGCCCTG CCTACTTTTA      1320
GTTGACTCAC AGGCCCTGGA GAAGCAGCTA ACAATGTCTG GTTAGTTAAA AGCCCATTGC      1380
CATTTGGTCT GGATTTTCTA CTGTAAGAAG AGCCATAGCT GATCATGTCC CCCTGACCCT      1440
TCCCTTCTTT TTTTATGCTC GTTTCGCTG GGATGGAAT TATTGTACCA TTTTCTATCA        1500
TGGAATATTT ATAGGCCAGG GCATGTGTAT GTGTCTGCTA ATGTAAACTT TGTCATGGTT      1560
TCCATTTACT AACAGCAACA GCAAGAAATA AATCAGAGAG CAAGGCATCG GGGGTGAATC      1620
TTGTCTAACA TTCCCGAGGT CAGCCAGGCT GCTAACCTGG AAAGCAGGAT GTAGTTCTGC      1680
CAGGCAACTT TTAAAGCTCA TGCATTTCAA GCAGCTGAAG AAAGAATCAG AACTAACCAG      1740
TACCTCTGTA TAGAAATCTA AAAGAATTTT ACCATTCAGT TAATTCAATG TGAACACTGG      1800
CACACTGCTC TTAAGAAACT ATGAAGATCT GAGATTTTTT TGTGTATGTT TTTGACTCTT      1860
TTGAGTGGTA ATCATATGTG TCTTTATAGA TGTACATACC TCCTTGCACA AATGGAGGGG      1920
AATTCATTTT CATCACTGGG ACTGTCCTTA GTGTATAAAA ACCATGCTGG TATATGGCTT      1980
CAAGTTGTAA AAATGAAAGT GACTTAAAA GAAAATAGGG GATGGTCCAG GATCTCCACT       2040
GATAAGACTG TTTTTAAGTA ACTTAAGGAC CTTTGGGTCT ACAAGTATAT GTGAAAAAAA      2100
TGAGACTTAC TGGGTGAGGA AATCCATTGT TTAAAGATGG TCGTGTGTGT GTGTGTGTGT      2160
GTGTGTGTGT TGTGTTGTGT TTTGTTTTTT AAGGGAGGGA ATTTATTATT TACCGTTGCT      2220
TGAAATTACT GTGTAAATAT ATGTCTGATA ATGATTTGCT CTTTGACAAC TAAAATTAGG      2280
ACTGTATAAG TACTAGATGC ATCACTGGGT GTTGATCTTA CAAGATATTG ATGATAACAC      2340
TTAAAATTGT AACCTGCATT TTTCACTTTG CTCTCAATTA AAGTCTATTC AAAAGGAAAA      2400
AAAAAAAAA AA                                                           2412
```

( 2 ) INFORMATION FOR SEQ ID NO:19:

( i ) SEQUENCE CHARACTERISTICS:
        ( A ) LENGTH: 268 base pairs
        ( B ) TYPE: nucleic acid
        ( C ) STRANDEDNESS: single
        ( D ) TOPOLOGY: linear ( i i ) MOLECULE TYPE: cDNA to mRNA(genomic)

( x i ) SEQUENCE DESCRIPTION: SEQ ID NO:19:

-continued

```
TCCTACAGCC AAGCTCCAAG TCAATATAGC CAACAGAGCA GCAGCTACGG GCAGCAGAGT      60

GAGAAACCAT ACCAGTGTGA CTTCAAGGAC TGTGAACGAA GGTTTTCTCG TTCAGACCAG     120

CTCAAAAGAC ACCAAGGAG ACATACAGGT GTGAAACCAT TCCAGTGTAA AACTTGTCAG      180

CGAAAGTTCT CCCGGTCCGA CCACCTGAAG ACCCACACCA GGACTCATAC AGGTAAAACA     240

AGTGAAAAGC CCTTCAGCTG TCGGTGGC                                        268
```

(2) INFORMATION FOR SEQ ID NO:20:

(i) SEQUENCE CHARACTERISTICS:
    (A) LENGTH: 365 amino acids
    (B) TYPE: amino acid
    (C) STRANDEDNESS: unknown
    (D) TOPOLOGY: unknown (ii) MOLECULE TYPE: protein (xi) SEQUENCE DESCRIPTION: SEQ ID NO:20:

```
Met Ala Ser Thr Asp Tyr Ser Thr Tyr Ser Gln Ala Ala Gln Gln
  1               5                  10                  15

Gly Tyr Ser Ala Tyr Thr Ala Gln Pro Thr Gln Gly Tyr Ala Gln Thr
                 20                  25                  30

Thr Gln Ala Tyr Gly Gln Gln Ser Tyr Gly Thr Tyr Gly Gln Pro Thr
             35                  40                  45

Asp Val Ser Tyr Thr Gln Ala Gln Thr Thr Ala Thr Tyr Gly Gln Thr
 50                  55                  60

Ala Tyr Ala Thr Ser Tyr Gly Gln Pro Pro Thr Gly Tyr Thr Thr Pro
 65                  70                  75                  80

Thr Ala Pro Gln Ala Tyr Ser Gln Pro Val Gln Gly Tyr Gly Thr Gly
                 85                  90                  95

Ala Tyr Asp Thr Thr Thr Ala Thr Val Thr Thr Thr Gln Ala Ser Tyr
                100                 105                 110

Ala Ala Gln Ser Ala Tyr Gly Thr Gln Pro Ala Tyr Pro Ala Tyr Gly
             115                 120                 125

Gln Gln Pro Ala Ala Thr Ala Pro Thr Arg Pro Gln Asp Gly Asn Lys
130                 135                 140

Pro Thr Glu Thr Ser Gln Pro Gln Ser Ser Thr Gly Gly Tyr Asn Gln
145                 150                 155                 160

Pro Ser Leu Gly Tyr Gly Gln Ser Asn Tyr Ser Tyr Pro Gln Val Pro
                165                 170                 175

Gly Ser Tyr Pro Met Gln Pro Val Thr Ala Pro Pro Ser Tyr Pro Pro
                180                 185                 190

Thr Ser Tyr Ser Ser Thr Gln Pro Thr Ser Tyr Asp Gln Ser Ser Tyr
            195                 200                 205

Ser Gln Gln Asn Thr Tyr Gly Gln Pro Ser Ser Tyr Gly Gln Gln Ser
210                 215                 220

Ser Tyr Gly Gln Gln Ser Ser Tyr Gly Gln Gln Pro Pro Thr Ser Tyr
225                 230                 235                 240

Pro Pro Gln Thr Gly Ser Tyr Ser Gln Ala Pro Ser Gln Tyr Ser Gln
                245                 250                 255

Gln Ser Ser Ser Tyr Gly Gln Gln Ser Glu Lys Pro Tyr Gln Cys Asp
            260                 265                 270

Phe Lys Asp Cys Glu Arg Arg Phe Ser Arg Ser Asp Gln Leu Lys Arg
            275                 280                 285

His Gln Arg Arg His Thr Gly Val Lys Pro Phe Gln Cys Lys Thr Cys
290                 295                 300
```

| Gln | Arg | Lys | Phe | Ser | Arg | Ser | Asp | His | Leu | Lys | Thr | His | Thr | Arg | Thr |
| 305 | | | | | 310 | | | | | 315 | | | | | 320 |

| His | Thr | Gly | Lys | Thr | Ser | Glu | Lys | Pro | Phe | Ser | Cys | Arg | Trp | Pro | Ser |
| | | | | 325 | | | | | 330 | | | | | 335 | |

| Cys | Gln | Lys | Lys | Phe | Ala | Arg | Ser | Asp | Glu | Leu | Val | Arg | His | His | Asn |
| | | | 340 | | | | | 345 | | | | | 350 | | |

| Met | His | Gln | Arg | Asn | Met | Thr | Lys | Leu | Gln | Leu | Ala | Leu |
| | | 355 | | | | 360 | | | | | | 365 |

( 2 ) INFORMATION FOR SEQ ID NO:21:

( i ) SEQUENCE CHARACTERISTICS:
        ( A ) LENGTH: 362 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:21:

| Met | Ala | Ser | Thr | Asp | Tyr | Ser | Thr | Tyr | Ser | Gln | Ala | Ala | Ala | Gln | Gln |
| 1 | | | | 5 | | | | | 10 | | | | | 15 | |

| Gly | Tyr | Ser | Ala | Tyr | Thr | Ala | Gln | Pro | Thr | Gln | Gly | Tyr | Ala | Gln | Thr |
| | | | 20 | | | | | 25 | | | | | 30 | | |

| Thr | Gln | Ala | Tyr | Gly | Gln | Gln | Ser | Tyr | Gly | Thr | Tyr | Gly | Gln | Pro | Thr |
| | | 35 | | | | | 40 | | | | | 45 | | | |

| Asp | Val | Ser | Tyr | Thr | Gln | Ala | Gln | Thr | Thr | Ala | Thr | Tyr | Gly | Gln | Thr |
| | 50 | | | | | 55 | | | | | 60 | | | | |

| Ala | Tyr | Ala | Thr | Ser | Tyr | Gly | Gln | Pro | Pro | Thr | Gly | Tyr | Thr | Thr | Pro |
| 65 | | | | | 70 | | | | | 75 | | | | | 80 |

| Thr | Ala | Pro | Gln | Ala | Tyr | Ser | Gln | Pro | Val | Gln | Gly | Tyr | Gly | Thr | Gly |
| | | | | 85 | | | | | 90 | | | | | 95 | |

| Ala | Tyr | Asp | Thr | Thr | Thr | Ala | Thr | Val | Thr | Thr | Thr | Gln | Ala | Ser | Tyr |
| | | | 100 | | | | | 105 | | | | | 110 | | |

| Ala | Ala | Gln | Ser | Ala | Tyr | Gly | Thr | Gln | Pro | Ala | Tyr | Pro | Ala | Tyr | Gly |
| | | 115 | | | | | 120 | | | | | 125 | | | |

| Gln | Gln | Pro | Ala | Ala | Thr | Ala | Pro | Thr | Arg | Pro | Gln | Asp | Gly | Asn | Lys |
| | 130 | | | | | 135 | | | | | 140 | | | | |

| Pro | Thr | Glu | Thr | Ser | Gln | Pro | Gln | Ser | Ser | Thr | Gly | Gly | Tyr | Asn | Gln |
| 145 | | | | | 150 | | | | | 155 | | | | | 160 |

| Pro | Ser | Leu | Gly | Tyr | Gly | Gln | Ser | Asn | Tyr | Ser | Tyr | Pro | Gln | Val | Pro |
| | | | | 165 | | | | | 170 | | | | | 175 | |

| Gly | Ser | Tyr | Pro | Met | Gln | Pro | Val | Thr | Ala | Pro | Pro | Ser | Tyr | Pro | Pro |
| | | | 180 | | | | | 185 | | | | | 190 | | |

| Thr | Ser | Tyr | Ser | Ser | Thr | Gln | Pro | Thr | Ser | Tyr | Asp | Gln | Ser | Ser | Tyr |
| | | 195 | | | | | 200 | | | | | 205 | | | |

| Ser | Gln | Gln | Asn | Thr | Tyr | Gly | Gln | Pro | Ser | Ser | Tyr | Gly | Gln | Gln | Ser |
| | 210 | | | | | 215 | | | | | 220 | | | | |

| Ser | Tyr | Gly | Gln | Gln | Ser | Ser | Tyr | Gly | Gln | Gln | Pro | Pro | Thr | Ser | Tyr |
| 225 | | | | | 230 | | | | | 235 | | | | | 240 |

| Pro | Pro | Gln | Thr | Gly | Ser | Tyr | Ser | Gln | Ala | Pro | Ser | Gln | Tyr | Ser | Gln |
| | | | | 245 | | | | | 250 | | | | | 255 | |

| Gln | Ser | Ser | Ser | Tyr | Gly | Gln | Gln | Ser | Glu | Lys | Pro | Tyr | Gln | Cys | Asp |
| | | | 260 | | | | | 265 | | | | | 270 | | |

| Phe | Lys | Asp | Cys | Glu | Arg | Arg | Phe | Ser | Arg | Ser | Asp | Gln | Leu | Lys | Arg |
| | | 275 | | | | | 280 | | | | | 285 | | | |

| His | Gln | Arg | Arg | His | Thr | Gly | Val | Lys | Pro | Phe | Gln | Cys | Lys | Thr | Cys |

-continued

|  | 290 |  |  |  |  | 295 |  |  |  | 300 |  |  |  |  |
|---|---|---|---|---|---|---|---|---|---|---|---|---|---|---|
| Gln 305 | Arg | Lys | Phe | Ser | Arg 310 | Ser | Asp | His | Leu | Lys 315 | Thr | His | Thr | Arg | Thr 320 |
| His | Thr | Gly | Glu | Lys 325 | Pro | Phe | Ser | Cys | Arg 330 | Trp | Pro | Ser | Cys | Gln 335 | Lys |
| Lys | Phe | Ala | Arg 340 | Ser | Asp | Glu | Leu | Val 345 | Arg | His | His | Asn | Met 350 | His | Gln |
| Arg | Asn | Met 355 | Thr | Lys | Leu | Gln | Leu 360 | Ala | Leu |  |  |  |  |  |  |